US009200258B2

(12) United States Patent
Mezghanni et al.

(10) Patent No.: US 9,200,258 B2
(45) Date of Patent: Dec. 1, 2015

(54) MULTICELLULAR ORGANOTYPIC MODEL OF HUMAN INTESTINAL MUCOSA

(75) Inventors: Rosangela Mezghanni, Ellicott City, MD (US); Alessio Fasano, West Friendship, MD (US); Marcelo Sztein, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 20 days.

(21) Appl. No.: 13/360,539

(22) Filed: Jan. 27, 2012

(65) Prior Publication Data

US 2012/0196275 A1  Aug. 2, 2012

Related U.S. Application Data

(60) Provisional application No. 61/436,710, filed on Jan. 27, 2011.

(51) Int. Cl.
*C12N 5/071* (2010.01)
*C12Q 1/02* (2006.01)
*G01N 33/50* (2006.01)

(52) U.S. Cl.
CPC ............ *C12N 5/0679* (2013.01); *C12N 5/0697* (2013.01); *C12Q 1/02* (2013.01); *G01N 33/5005* (2013.01); *C12N 2500/25* (2013.01); *C12N 2501/01* (2013.01); *C12N 2501/115* (2013.01); *C12N 2501/125* (2013.01); *C12N 2501/235* (2013.01); *C12N 2501/365* (2013.01); *C12N 2501/395* (2013.01); *C12N 2501/91* (2013.01); *C12N 2502/1323* (2013.01); *C12N 2502/23* (2013.01); *C12N 2502/28* (2013.01); *C12N 2503/04* (2013.01); *C12N 2513/00* (2013.01); *C12N 2525/00* (2013.01); *C12N 2533/52* (2013.01); *C12N 2533/54* (2013.01)

(58) Field of Classification Search
None
See application file for complete search history.

(56) References Cited

U.S. PATENT DOCUMENTS 5,496,722 A * 3/1996 Goodwin et al. ............. 435/371
7,217,570 B2 * 5/2007 Herlyn et al. ................. 435/397

OTHER PUBLICATIONS

BD™ Biosciences "BD™ MATRIGEL™ Basement Membrane Matrix" Online Catalog, available online 2013.*
BD™ Biosciences "BD™ MATRIGEL™ matrix frequently asked questions" Online Documents, available online 2011.*
Unsworth et al. "Growing tissues in microgravity" Nature Medicine 4(8): 901-907, 1998.*
Partap et al. "Chapter 16: Bioreactors in tissue engineering", Tissue Engineering, ed. Daniel Eberli, InTech: 323-36, published online Mar. 2010.*
Warren et al. "Detection of epithelial-cell injury, and quantification of infection, in the HCT-8 organoid model of Cryptosporidiosis", Journal of Infectious Diseases 198: 143-9, 2008.*
Bisping et al. "Patients with inflammatory bowel disease (IBD) reveal increased induction capacity of intracellular interferon-gamma (IFN-gamma) in peripheral CD8+ lymphocytes co-cultured with intestinal epithelial cells", Clinical Experimental Immunology 123(1): 15-22, 2001.*
Cornwell et al. "Extracellular matrix biomaterials for soft tissue repair." Clinics in Podiatric Medicine and Surgery 26 (4): 507-523, 2009.*

* cited by examiner

*Primary Examiner* — Taeyoon Kim
*Assistant Examiner* — Emily Cordas
(74) *Attorney, Agent, or Firm* — Kristina Castellano; Castellano PLLC

(57) ABSTRACT

Disclosed are methods of preparing multi-cellular three-dimensional tissue constructs, that include fibroblasts, endothelial cells, lymphocytes and epithelial cells. The present methods may include embedding fibroblasts and endothelial cells in a matrix enriched with gut basement membrane proteins to form a cell containing matrix that is then added to a bioreactor and exposed to epithelial cells and activated lymphocytes as the cell cultures. Also provided are the tissue constructs formed from such methods, a matrix enriched with gut basement membrane proteins and kits that include the same. Further provided are methods of measuring toxicity of a pathogen or commensal organisms, chemosensitivity of tissues to a toxic material and inflammatory conditions, which use the present multi-cellular three-dimensional tissue constructs.

8 Claims, 16 Drawing Sheets

3-D Model

Normal human intestine epithelium

Figure 1. Diagram of the construction of the 3-D Model

FIG. 6
A
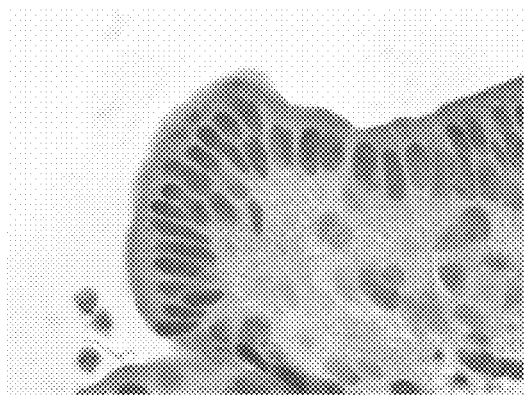
B
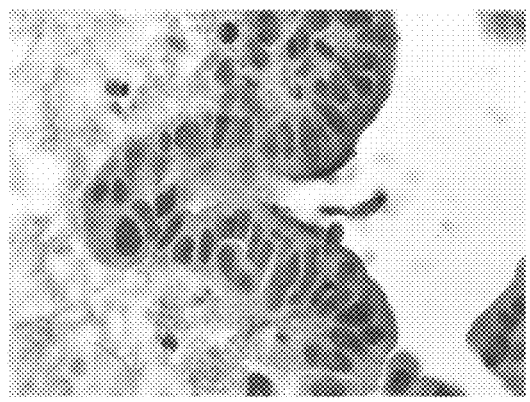
C
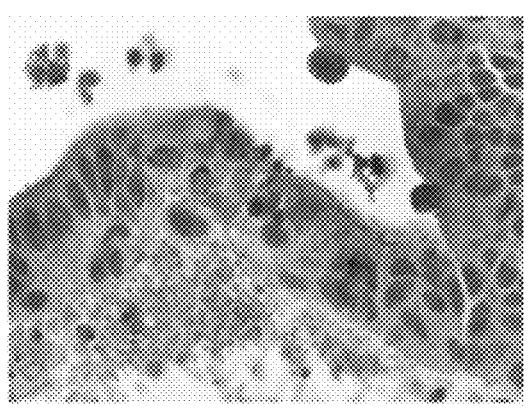

FIG. 11
(a)
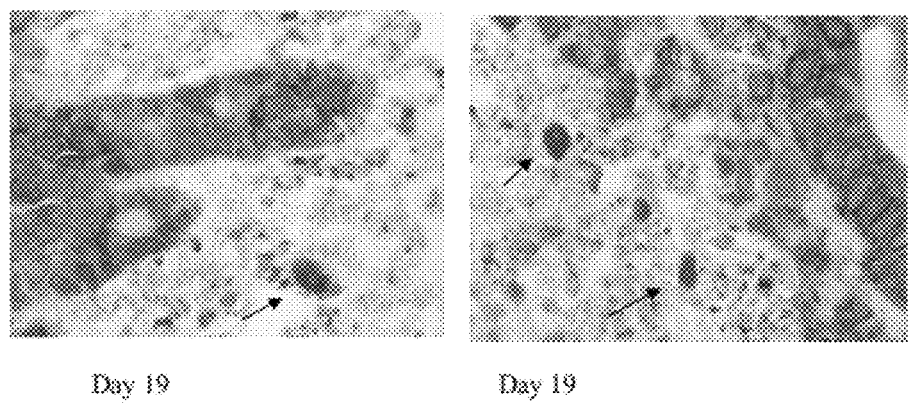
(b)
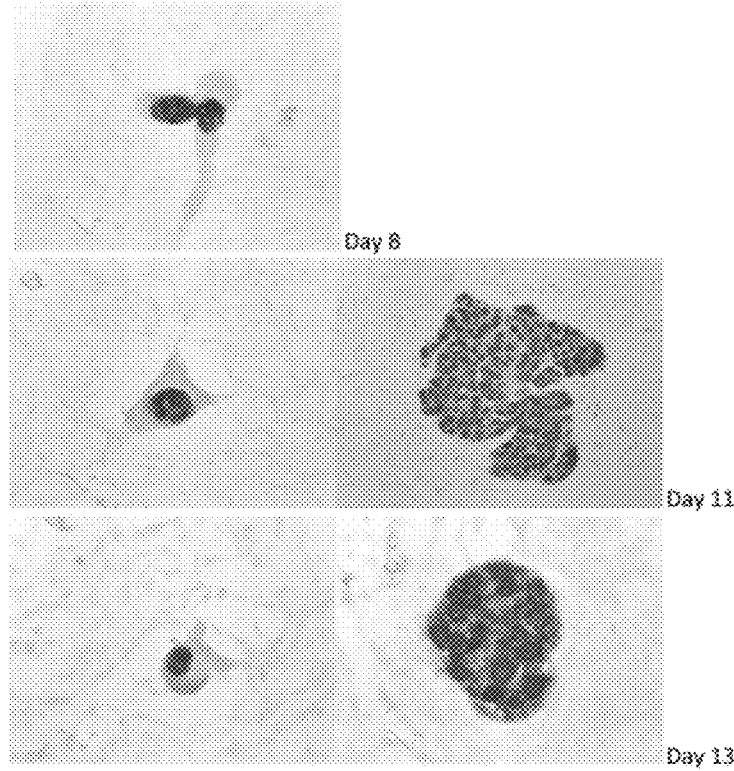

FIG. 17
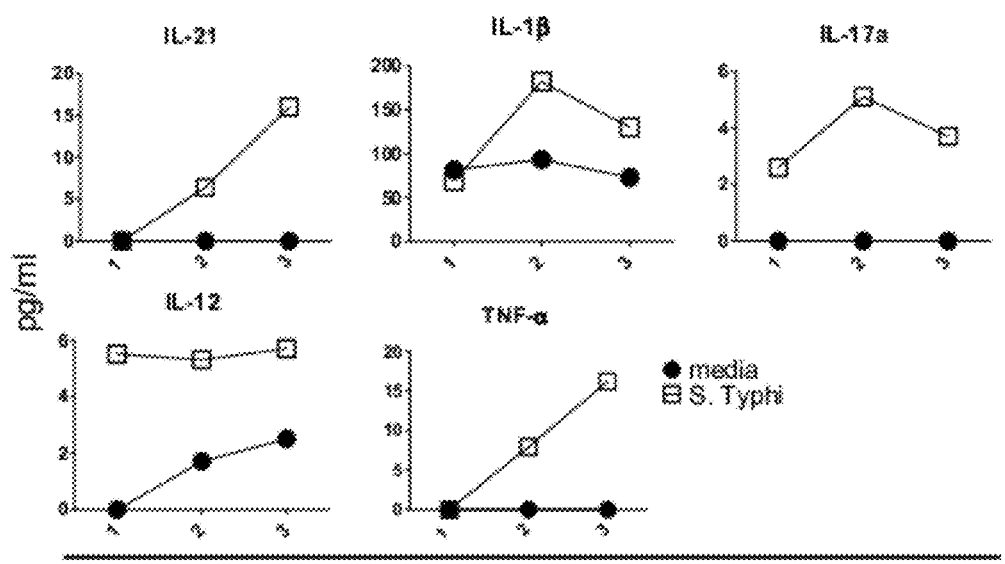
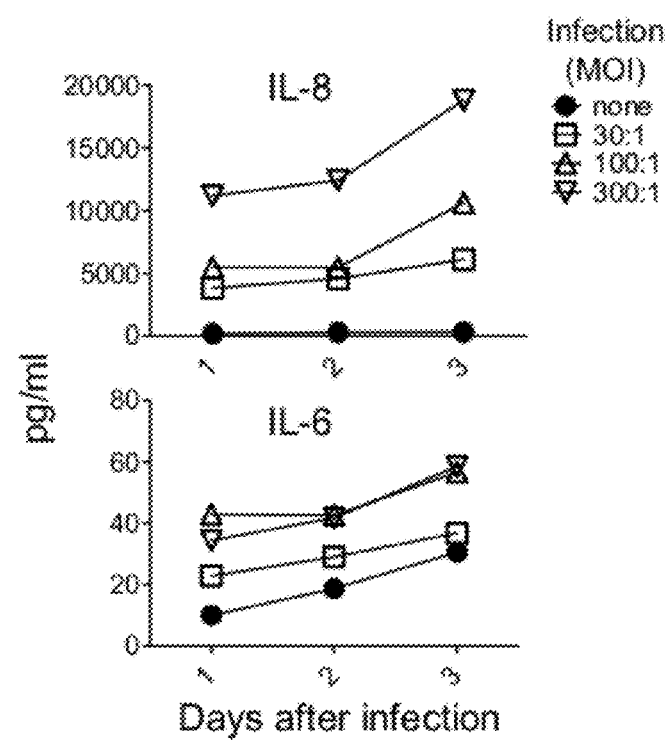

MULTICELLULAR ORGANOTYPIC MODEL OF HUMAN INTESTINAL MUCOSA

RELATED APPLICATION

This application claims the benefit of U.S. Provisional Application No. 61/436,710 filed on Jan. 27, 2011, the entire contents of which are hereby incorporated by reference in their entirety.

STATEMENT REGARDING FEDERALLY SPONSORED RESEARCH

This invention was made with government support under Grant Numbers AI030028, AI082655, AI036525, and DK048373 awarded by the National Institutes of Health. The government has certain rights in the invention.

FIELD

The present invention generally relates at least to the fields of microbiology, infectious disease, stem cell biology, diseases with an immunological component (e.g., autoimmunity) and drug toxicity. In particular, the present invention relates to methods of preparing multicellular, three-dimensional tissue constructs of mammalian cells and for modeling infectious, autoimmune, inflammatory and other diseases and chemosensitivity using the three-dimensional tissue constructs of cells.

BACKGROUND

The engineering of multicellular organotypic models of the human intestinal mucosa has wide-ranging potential as a tool for discovery in both health and disease, including interaction with pathogens, antigen trafficking, inflammatory and physiological processes as well as tissue bioengineering. However, models reported to date remain relatively simple composed of few cell types. In particular, prior models consist of: (1) small fragments of human primary tissues which can be maintained in vitro for a very short time, or (2) bioengineered tissues composed of a few different cell types, mainly epithelial cells and fibroblasts, but lacking other stromal cells (e.g., immune cells such as lymphocytes, macrophages and dendritic cells).

For example, U.S. Pat. No. 7,244,578 (Hammond), which is hereby incorporated herein by reference, provides methods for utilizing a form of suspension culture to examine infectivity of pathogenic organisms and agents. But among the many disadvantages of Hammond, Hammond uses extracellular matrix beads, which cannot be manipulated. Cells cannot be incorporated on the ECM of Hammond, and therefore Hammond's model cannot result in a multicellular ECM.

To more appropriately mimic an in vivo microenvironment, 3-dimensional cell culture models need to assume a more complex cellular architecture and functionalities which more closely resemble those observed in native tissues.

SUMMARY

The present inventors have developed an organotypic model structurally and functionally resembling the human intestinal mucosa comprised of epithelial, fibroblasts, lymphocytes and endothelial cells.

According to non-limiting example embodiments, the present invention relates to methods of preparing multi-cellular three-dimensional tissue constructs that include embedding fibroblasts and endothelial cells in a matrix enriched with one or more gut basement membrane proteins, to form a cell-containing matrix; contacting the cell-containing matrix with epithelial cells and culture medium in a bioreactor to form a cell culture; and allowing the cells to culture, while adding primary human lymphocytes to the cell culture, to form a multi-cellular three-dimensional tissue construct comprising a human intestinal epithelial cell line, primary human lymphocytes, endothelial cells and fibroblasts. Embodiments also relate to multi-cellular three-dimensional tissue constructs made by the present methods.

Example embodiments also relate to other three-dimensional multi-cellular tissue constructs that include a human intestinal epithelial cell line, primary human lymphocytes, endothelial cells and fibroblasts.

Example embodiments are also directed to a matrix comprising collagen I enriched with one or more gut basement membrane proteins, which may include e.g., one or more gut basement membrane proteins selected from the group consisting of laminin, collagen IV, fibronectin and heparan sulfate proteoglycans.

Additional example embodiments are directed to kits that may include a matrix, such as bovine collagen I enriched with gut basement membrane proteins; and at least one apparatus for performing the present methods such as one or more tissue culture flasks, culture plates, and a rotating wall vessel bioreactor, and/or instructions for performing the present methods.

Further embodiments are directed to methods of studying host interactions with an enteric pathogen in tissues, which include preparing a multi-cellular three-dimensional tissue construct, introducing an infectious enteric pathogen to the multi-cellular three-dimensional tissue construct; and assaying the infectivity of the infectious enteric pathogen.

Further embodiments are directed to methods of studying host responses to inflammatory stimuli, which include preparing a multi-cellular three-dimensional tissue construct, introducing agents or soluble factors (e.g., cytokines, chemokines) to the multi-cellular three-dimensional tissue construct; and assaying the effects of inflammatory stimuli on the multi-cellular three-dimensional tissue construct Further embodiments are directed to methods of studying intestinal stem cell biology and function in health and disease, which include preparing a multi-cellular three-dimensional tissue construct, isolation and culture on intestinal crypt cells, using specific markers to identify stem cells in the crypt niche, introducing agents or stimuli to the multi-cellular three-dimensional tissue construct; and assaying the effects of these variables in expansion and differentiation of intestinal stem cells Further embodiments are directed to methods of measuring chemosensitivity of tissues to a toxic material, which include preparing a multi-cellular three-dimensional tissue construct, introducing a toxic material to the multi-cellular three-dimensional tissue construct; and assaying the chemosensitivity of the toxic material.

BRIEF DESCRIPTION OF THE FIGURES

Non-limiting example embodiments are described herein, with reference to the following accompanying Figures:

FIG. 6(A-C) depicts immunochemical staining of 12 day-cells cultured in the 3-D microgravity model. Cells were infected with *Shigella flexneri* and immunochemical stained for *Shigella* antigens using anti-*Shigella* mAbs.

FIG. 11(A-B) depicts the ability to differentiate Stem Cells in the 3-D model. Cells were stained with Sox 9 antibodies which detect Sox9 antigens characteristic of primitive gut epithelial cells.

FIG. 17(A-B) depicts changes in epithelial cell morphology and cytokine production at different times after *Salmonella enterica* serovar *Typhi* (*S. Typhi*) infection.

DETAILED DESCRIPTION

The present inventors have developed in vitro organotypic models by using three-dimensional (3-D) cell cultures that will, e.g., facilitate studies of the human intestinal mucosa. The inventors describe herein the building of a 3-D organotypic system (e.g., of human intestinal mucosa) comprised of multiple cell types including epithelial cell lines, as well as primary human lymphocytes, fibroblasts and endothelial cells.

There is a great need for the development of new technologies such as the present 3-D cell cultures, which will facilitate studies of the human intestinal mucosa, as animal studies and studies from human specimens are not sufficient. Animal models are flawed in that they might not fully recapitulate human mucosal biology. Studies from human specimens (such as mucosal biopsies) are limited in availability and are restricted by particular experimental protocols.

It is very difficult however, to form a 3-D model that closely mimics native tissues because many factors may affect tissue models. For example, the following factors may make a difference in tissue models: nutrients and gas exchange; growth factors; 3-D cell-to-cell and cell-to-extracellular matrix (ECM) interactions; the type of ECM; and spatial orientation (e.g., similar to that found in the native mucosa).

Figure 1:
FIG. 1. depicts a normal human intestine epithelium.

FIG. 1 depicts a normal human intestine epithelium. As shown in FIG. 1, the mucosa of the small intestine is lined by simple columnar epithelium composed primarily of absorptive cells (enterocytes) and goblet cells. The present models are a major innovation over other available three-dimensional organotypic systems, particularly of the human intestinal epithelium.

Previous attempted models involve very basic, simple models that in many cases are composed of one or two cell types. For example, other models may include epithelial cells and fibroblasts but lack stromal cells such as cells from immune system (e.g., lymphocytes) and endothelial cells. In contrast, the present 3-dimensional organotypic models of, e.g., the human intestinal mucosa, include multiple cell types. To the inventors' knowledge, previous attempts to integrate multiple types of cells in 3-D constructs have been unsuccessful. Unlike other three dimensional models of the intestinal mucosa in which epithelial cells formed multiple layers or aggregates; the present system has the ability to mimic the monolayer organization of the gut epithelial cells. That is, the models of the present invention closely mimic the biology of, e.g., human intestinal mucosal and overcome many of the limitations of earlier models. To more appropriately mimic an in vivo microenvironment, three dimensional cell culture models need to assume a more complex cellular architecture and functions, which both structurally and functionally resemble the human intestinal mucosa.

Prior models may be for example an aggregate of cells, not a morphology like what is found in vivo. A drawback from this is the impossibility of having e.g., in situ observations of dynamic events of enteric pathogen infection or cell migration into the extra cellular matrix (ECM).

The present models also make the production of cytokines possible upon antigenic stimulation.

The present models include multiple cell types including: primary human lymphocytes, fibroblasts and endothelial cells as well as epithelial cell lines. Data gathered by the present inventors strongly suggests that the epithelial cells of the model are able to absorb and transport glucose. This epithelial line also behaves as a multi-potent progenitor cell that gives rise to functional and highly-differentiated cells from multiple lineages (i.e., absorptive enterocyte, goblet and M cells). Moreover, these cells interact with different biological components in a physiologically relevant manner. Epithelial cells in the present model have a spatial orientation similar to that found in the native mucosa. Bacteria in the present model will be located at the "lumen" side. Thus, in the present 3-D model bacteria will only be able to access the apical pole of epithelial cells, as it would happen in vivo. Further access to the extracellular matrix (ECM) will only occur if the bacteria actively breach the epithelial monolayer. Indeed, the growth pattern of this epithelial cell line was found to be similar to the normal epithelium. Epithelial cell lines expressed E-cadherin but only negligible amount of Ki-67 proliferation marker, a pattern consistent with normal highly-differentiated epithelium.

Further, the present models provide a long term culture with high viability of the primary cells. Cell viability in the present model was observed up to 20 days or longer after the initiation of the cultures. For example, at day 35, histological stainings with Hematoxylin and eosin (H&E) showed good morphology of cells with an intact matrix. According to non-limiting example embodiments, at 46 days one may start to see degradation of the extracellular matrix. These features allow for future developments such as the inclusion of bioengineered blood conduits. Ideally, in vitro 'organotypic models' will include blood vessel like conduits to facilitate delivery of oxygen and nutrients, the integration of endothelial cells into the present 3-D model opens the door for the creation of bioengineered blood conduits in a 3-D model composed of multiple cell types.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

All publications mentioned in this specification are indicative of the level of those skilled in the art to which the invention pertains. All patents and publications herein are incorporated by reference to the same extent as if each individual publication was specifically and individually indicated as having been incorporated by reference in its entirety.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

The various cells discussed herein (e.g., fibroblasts, endothelial cells and epithelial cells) may be "isolated", which may include e.g., growing the cells as a standard monolayer in tissue culture flasks apart from other cells, or they may include cells directly isolated from a human individual (e.g., stem cell).

The present invention provides a 3-D model having the following composition: lymphocytes, fibroblasts, intestinal epithelial cells, and endothelial cells, all linked to an extracellular matrix (ECM).

As indicated above, the present inventors have development an organotypic model with close structural and functional resemblance to the human intestinal mucosa; which model includes fibroblasts, lymphocytes, epithelial cells, and endothelial cells. Moreover, epithelial cells in the present 3-D system can differentiate into multiple lineages (e.g., goblet cells, M cells and differentiated enterocytes).

The present inventors hypothesized that under both microgravity and proper culture conditions, aggregates of randomly distributed cells will self-organize into a spatial configuration resembling those in native tissues. The inventors' hypothesis was based on recent developments showing that: (1) the culture of epithelial cells as well as endothelial cells under microgravity can be accompanied by a commensurate increase in the cell differentiation and (2) gelled collagen-I can constitute a flexible extracellular matrix (ECM) to be used under microgravity.

Non-limiting example embodiments of the present invention include methods of preparing multi-cellular three-dimensional tissue constructs that include lymphocytes, fibroblasts, epithelial cells and endothelial cells. Such methods include embedding fibroblasts and endothelial cells in a matrix to form a cell-containing matrix; combining the cell-containing matrix with epithelial cells and culture medium in a bioreactor to form a cell culture, and applying conditions in the bioreactor that minimize shear force inside the culture. The cells are then allowed to culture, while adding activated lymphocytes to the cell culture during the culture, to form a multi-cellular three-dimensional tissue construct.

The selected extracellular matrix (ECM) is important for several reasons. The ECM provides mechanical support; and influences cell adhesion, proliferation, differentiation, morphology, and gene expression. The ECM may also help immune cell migration into inflamed tissues.

Figure 3:
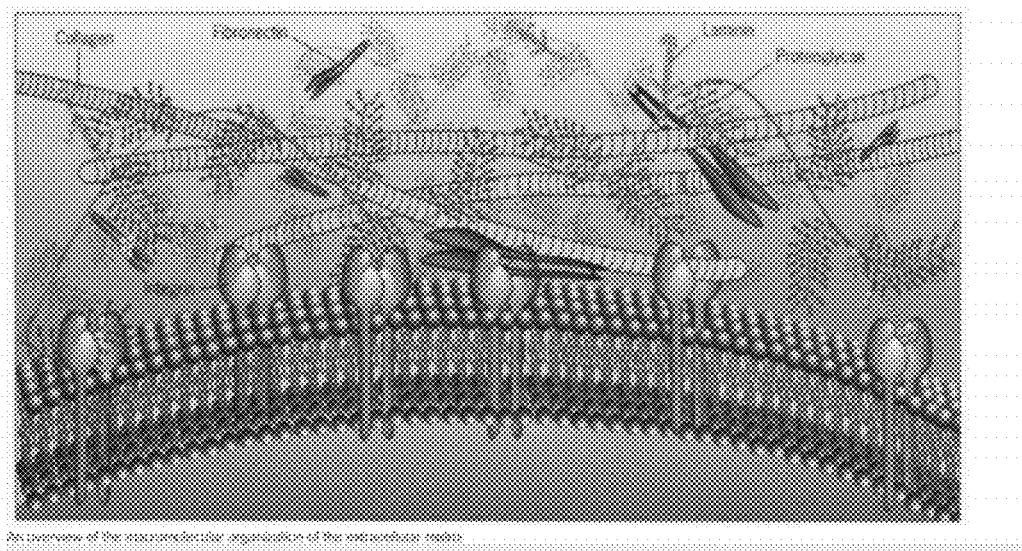
FIG. 3 depicts an overview of the macromolecular organization of the extracellular matrix enriched with gut basement membrane proteins in accordance with non-limiting example embodiments.

According to example embodiments, the matrix comprises collagen and/or another material having a specific gravity similar to the culture medium. The matrix may include collagen I for example. According to non-limiting example embodiments, the collagen matrix may be enriched with one or more gut basement membrane proteins. For example, such gut basement membrane proteins may include one or more of the following: laminin, collagen IV, fibronectin and heparan sulfate proteoglycans. Therefore, embodiments of the present invention also include a matrix that includes bovine collagen I enriched with one or more gut basement membrane proteins selected from the group consisting of laminin, collagen IV, fibronectin and heparan sulfate proteoglycans. FIG. 3 depicts an overview of the macromolecular organization of the extracellular matrix enriched with gut basement membrane proteins in accordance with non-limiting example embodiments.

The present models are different from prior attempted 3-D models, e.g., with respect to the matrix that is used. Prior 3-D models attempted to use beads or collagen sheets as extracellular matrix (ECM). However in such embodiments, the ECM cannot be manipulated, cells cannot be incorporated on the ECM, and therefore the prior model cannot have a multicellular ECM.

According to non-limiting example embodiments, the epithelial cells may include for example, one or more human cells selected from intestinal cells, lung cells, kidney cells, liver cells, bladder cells and stem cells. According to example embodiments, the epithelial cells include human epithelial cells from gastrointestinal segments. According to further embodiments, the epithelial cells include a human enterocyte cell line (HCT-8) derived from the junction of the small and large bowel.

Fibroblasts according to the present invention may include for example, human fibroblasts from gastrointestinal segments or tissues. Example fibroblasts may include primary human colonic fibroblasts.

Example endothelial cells may include for example, human endothelial cells from tissues. Non-limiting examples may include human umbilical vein endothelial cells (HUVEC).

A suitable culture medium may be selected by those skilled in the art and may include for example 3-D culture media: Ham's F-12 (INVITROGEN). According to example embodiments, the culture medium may be supplemented with at least one of gentamicin, fetal bovine serum, insulin, 3,3', 5-triiodo-L-thyronine (T3), adenine, transferrin, cholera toxin, glutamine, Leukemia Inhibitory Factor human (LIF), Stem Cell Factor, Endothelin 3 human and Fibroblast Growth Factor.

According to non-limiting example embodiments, the bioreactor may be for example, a rotating wall vessel (RWV) bioreactor, or other bioreactor that is capable of applying conditions that minimize or provide relatively low shear force inside the culture. The low shear force inside the culture is related to the speed and the size of the construct. For example, constructs might increase their size if there is cell proliferation. The bioreactor may also be one that produces conditions that produce laminar flow. Those skilled in the art using bioreactors would understand the conditions (e.g., microgravity conditions that product laminar flow and minimize shear force). Example cell culture conditions in an appropriate bioreactor under conditions of applied shear potentiate spatial co-localization and three-dimensional assembly of individual cells into large aggregates, which more closely resemble the in vivo tissue equivalent. In this environment, dissociated cells can assemble and differentiate into macroscopic tissue aggregates.

The use of microgravity bioreactors in the past has had some limitations. For example, prior constructs have been unable to incorporate stromal cells (e.g., Immune cells such as lymphocytes, macrophages and dendritic cells) and fibroblasts inside of the ECM. Indeed, the scaffolds for the RWV system, such as microbeads or small synthetic sheets, cannot have their composition manipulated. Additionally, the most common scaffolds such as matrigel used in stationary models, cannot be used in bioreactors. This is because the specific gravity of the scaffold is different than that of the culture medium. The scaffolds can be degraded or contracted too quickly.

According to non-limiting example embodiments, the cell culture may be up to about 24 days, or more, including e.g., up to about 35 days or up to about 46 days. By way of non-limiting example, the cell culture may be from about 12-22 days or about 14-18 days. According to non-limiting example embodiments, the lymphocytes (e.g., activated lymphocytes) may be added once, twice or even more times during the cell culture. For example, the lymphocytes may be added at approximately days 4 (±1 day) and 9 (±1 day)) of the cell culture. Thus, according to non-limiting example embodiments, the activated lymphocytes may be added to the cell culture at around day 3-5 and at around day 8-10. According to non-limiting embodiments, activated lymphocytes may be added to the cell culture at different points during the cell culture, for example they may be added only once, twice, or more than twice during the cell culture, and they may be added at a different day/time of the cell culture.

Figure 2:
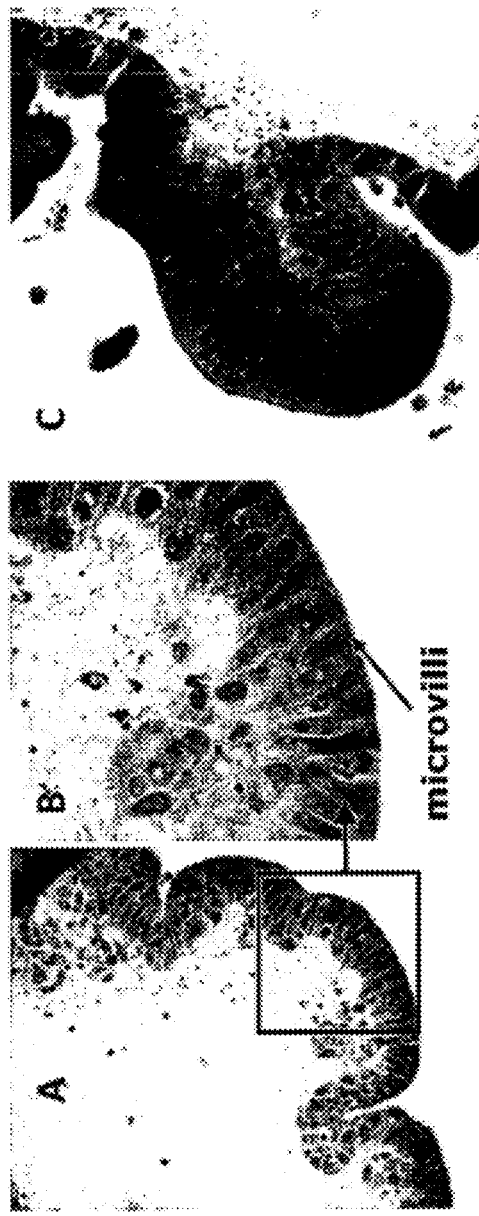
FIG. 2 depicts cells cultured in an example of the present 3-D microgravity models.

A further advantage of the present models over prior models is that embodiments of the present model may be created in a much shorter time, e.g., in 14 or 15 days; whereas other models may take e.g., 28-32 days to develop. FIG. 2 depicts the histology of cells cultured in an example embodiment of the present 3-D microgravity model. In particular, this Figure shows tissue stains and scaffold stains. The cells in FIG. 2 were cultured for 14 days (A) low and (B) higher magnification; and cultured for 20 days (C) higher magnification.

The present methods may also include placing the cell-containing matrix in a mold and allowing the cell-containing matrix to jellify prior to adding the cell-containing matrix to the bioreactor.

Example non-limiting embodiments, include preparing a multi-cellular three-dimensional tissue construct embedding isolated fibroblasts and isolated endothelial cells in a collagen matrix (such as collagen-I) that may be enriched with one or more gut basement membrane proteins to form a cell-containing matrix; adding the cell-containing matrix to a rotating wall vessel bioreactor containing human intestinal epithelial cells and culture medium to form a cell culture; applying microgravity conditions that produce laminar flow and minimize shear force inside the culture, allowing the cells to culture (e.g., for up to about 24 days), while adding primary human lymphocytes (e.g., activated lymphocytes) to the cell culture, to form a multi-cellular three-dimensional tissue construct comprising a human intestinal epithelial cell line, primary human lymphocytes, endothelial cells and fibroblasts. The gut basement membrane proteins may include for example, one or more of the following: laminin, collagen IV, fibronectin and heparan sulfate proteoglycans, or other gut basement proteins.

According to these embodiments, the epithelial cells, endothelial cells, fibroblasts, lymphocytes, matrix and other components may be for example as described hereinthroughout.

According to example embodiments, the multi-cellular three-dimensional organotypic model may be a multi-cellular three-dimensional organotypic model of human intestinal mucosa.

According to example embodiments the embedding step may include embedding stem cells in the collagen matrix (such as collagen-I).

Collagen-I possesses many properties of an ideal scaffold, such as specific gravity similar to the culture medium and the capability to incorporate other relevant ECM proteins. In the present model, fibroblasts and endothelial cells may be embedded in a collagen-I matrix enriched with additional gut basement membrane proteins (e.g., laminin, collagen IV, fibronectin and heparan sulfate proteoglycan) and added to a bioreactor, such as a Rotating Wall Vessel (RWV) bioreactor containing epithelial cells (See FIG. 4). These epithelial cells may be for example, human enterocyte cell line (e.g., HCT-8) that was originally derived from the junction of the small and large bowel. The choice of this cell line was based on its ability to successfully differentiate in a low shear microgravity environment provided by the RWV bioreactor. However, the degree of differentiation of this epithelial cell under others conditions was always lower than one obtained using inventor's methodology probably due to the lack of crosstalk with the other cell types. (Unsworth BR, Lelkes PI, "Growing tissues in microgravity," Nat Med 1998; 4:901-7.) Activated lymphocytes may be added twice to the culture at e.g., days 4 (±1 day) and 9 (±1 day) of the culture. But as indicated above, the lymphocytes may be added fewer or more times and/or at different days during the culture. The importance of cell-cell interactions in influencing intestinal cell survival and differentiation is well documented.

The present invention is also directed to three-dimensional multi-cellular tissue constructs comprising a human intestinal epithelial cell line, primary human lymphocytes, endothelial cells and fibroblasts.

Further embodiments herein are directed to three-dimensional multi-cellular tissue constructs made by any of the methods provided herein.

Figure 4:
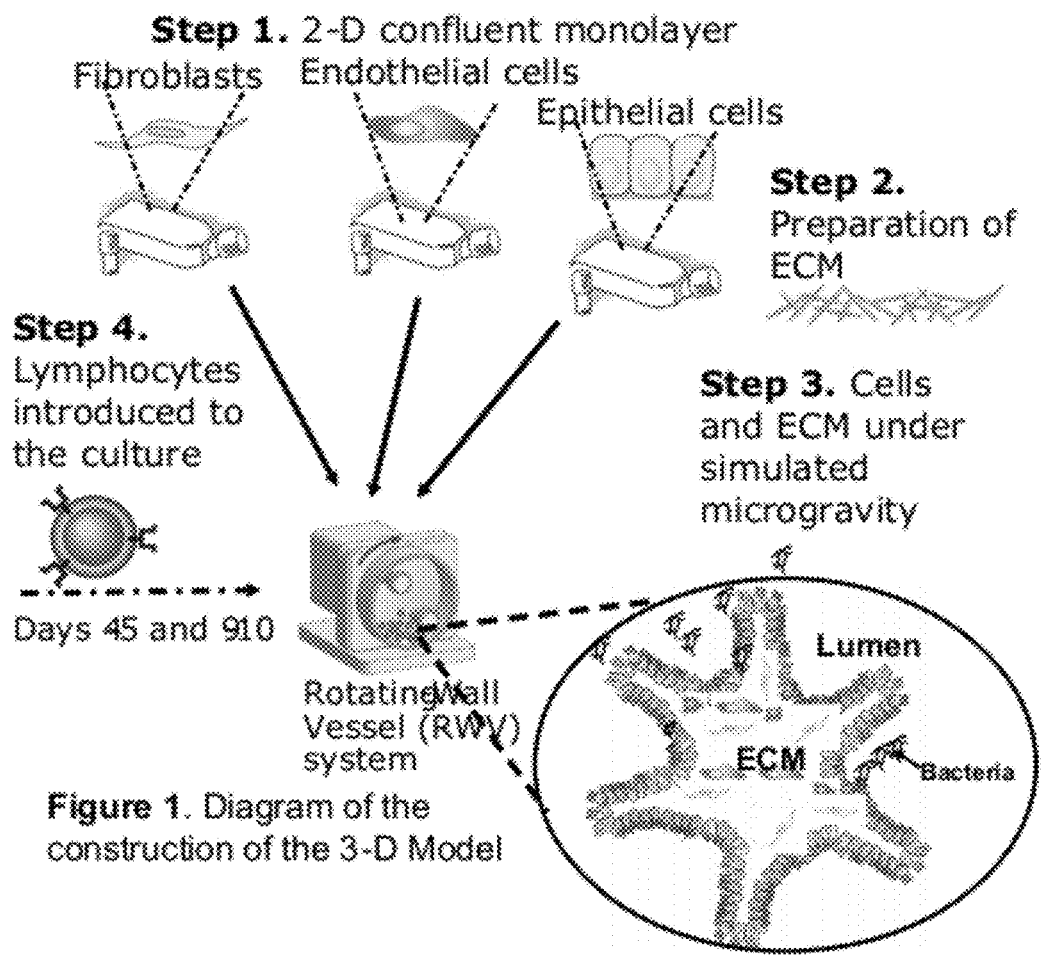
FIG. 4 depicts a diagram of the construction of a 3-D organotypic model of the human intestinal mucosa, in accordance with non-limiting embodiments.

Referring to FIG. 4, the Figure is a diagram of a non-limiting example of the construction of a 3-D organotypic model of the human intestinal mucosa, in accordance with non-limiting embodiments. The three cell types, i.e., fibroblasts, endothelial and epithelial cells, may be initially grown as standard monolayers in tissue culture flasks (step 1). After trypsinization, endothelial cells and fibroblasts may be resuspended in DMEM-30% FBS medium and added to an enriched collagen mixture. The collagen mixture may be of bovine collagen-I, collagen IV, fibronectin and heparan sulfate proteoglycans, for example (step 2). The cell-containing mixture may then be added to a mold, such as a 6 well-millicell culture plate insert (Millipore) and allowed to jellify. After the jellification step is completed, the cell-containing gel may be aseptically cut in small squares (about 5×5 mm) and transferred into the 50 ml rotating wall vessel (RWV) containing epithelial cells (step 3). After 4 days (+/−1 day) lymphocyte blasts may be added to each vessel and grown for an additional 5 days (+/−1 day) (step 4). At that time, blasts may be added once again to each vessel and the cultures continued for up to 12 additional days.

The present 3-D models may be used for example, to monitor at high resolution (e.g., in situ or by genomic or proteomic platforms) inflammatory responses, epithelial barrier functions and absorption and metabolism of drugs. The present models may include one or more of the following features: multiple constructs may be available at a specific time from one single 3-D model; induction of appropriate polarity of epithelial cells, tight junctions, desmosomes and microvilli; and long-term culture (up to e.g., 28 days) with high viability of the primary cells; transport of nutrients such as glucose (i.e., expression of dissacharidases, and presence of sugar transporters); multiple cell types: primary lymphocytes, endothelial cells and fibroblasts as well as epithelial cell lines.

The present models may also be useful for example, to monitor at high resolution the exposure to environmental and infectious agents such as an enteric pathogen (e.g., *Salmonella enterica* serovar *Typhi* (*S. Typhi*) and *Shigella flexneri*), as well as inflammatory mediators (e.g., cytokines, chemokines). Investigations into the interaction of *Salmonella* with the human intestinal epithelium have been limited by the lack of in vitro and in vivo models which replicate the in vivo condition. For example, conventional tissue culture technology has failed to yield high-fidelity, multicellular three-dimensional models of intestinal epithelium which are suitable for investigations into *Salmonella*-induced gastroenteritis.

Thus, also provided herein are methods of studying host interactions with a pathogen (such as an enteric pathogen) in tissues that include embedding isolated fibroblasts and isolated endothelial cells (and optionally stem cells) in a matrix (such as collagen-I) enriched with one or more gut basement membrane proteins to form a cell-containing matrix; combining the cell-containing matrix with epithelial cells and culture medium in a bioreactor (such as a rotating wall bioreactor) to form a cell culture, applying conditions that minimize shear force inside the culture allowing the cells to culture (e.g., for up to about 24 days), while adding lymphocytes (such as primary human lymphocytes) to the cell culture, to form a multi-cellular three-dimensional tissue construct; introducing an infectious pathogen to said multi-cellular three-dimensional tissue construct; and assaying the infectivity of said infectious pathogen. The assaying may include obtaining a measurement of, or observation of at least one parameter with respect to the multi-cellular three-dimensional tissue construct from which one could determine host interaction with the enteric pathogen.

The assaying may include obtaining a measurement of, or observation of at least one of the following parameters after introducing said infectious pathogen: changes in epithelial cell morphology; cytokine expression or production in cultured cells; expression of tissue-like differentiation markers; presence of alkaline phosphatase in cell lysate; adherence of said infectious pathogen to cultured cells; mRNA or protein expression in cultured cells; invasion of said pathogen into cultured cells; death or damage of cultured cells; and tissue pathology of aggregates of cultured cells.

Thus, by way of non-limiting example, provided herein are methods of studying host interactions with an enteric pathogen in tissues that include the following: embedding isolated fibroblasts and isolated endothelial cells in a collagen I matrix enriched with one or more gut basement membrane proteins to form a cell-containing matrix; adding the cell-containing matrix to a rotating wall vessel bioreactor containing human intestinal epithelial cells and culture medium to form a cell culture; applying microgravity conditions that produce laminar flow and low shear force inside the culture, allowing the cells to culture (e.g., for up to about 24 days), while adding activated primary human lymphocytes to the cell culture, to form a multi-cellular three-dimensional tissue construct comprising a human intestinal epithelial cell line, primary human lymphocytes, endothelial cells and fibroblasts; and introducing an infectious enteric pathogen to said multi-cellular three-dimensional tissue construct. The methods further include assaying the infectivity of said infectious enteric pathogen. The assaying may include for example, obtaining a measurement of, or observation of at least one of the following parameters after introducing said infectious pathogen: changes in epithelial cell morphology; cytokine expression or production in cultured cells; expression of tissue-like differentiation markers; presence of alkaline phosphatase in cell lysate; adherence of said infectious pathogen to cultured cells; mRNA or protein expression in cultured cells; invasion of said pathogen into cultured cells; death or damage of cultured cells; and tissue pathology of aggregates of cultured cells.

The term "infectious" "infectivity" and "infect" is used herein with respect to adherence to cells, invasion, survival within, and damage or destruction to cells.

According to non-limiting example embodiments, the enteric pathogen may be selected from the group consisting of viruses, bacteria, protozoa, parasites and fungi. The pathogen may include for example, a human enteric bacterial pathogen. The infectious pathogen may be selected for example, from one or more of the following pathogens: wild-type *Salmonella enterica* serovar *Typhi* (*S. Typhi*), *Shigella flexneri*, and *E. coli*. The model also accommodates the growth of probiotics, for example, *E. coli* strain Nissle 1917. The model also accommodates the growth of commensal organisms/microflora, for example *E. coli* strain BL-21.

According to non-limiting example embodiments, the enteric pathogen may be introduced within the bioreactor. According to other non-limiting example embodiments, the enteric pathogen is introduced outside the bioreactor. For example, the three-dimensional aggregates may be formed within the bioreactor and then infected with microorganisms outside the bioreactor environment (e.g. in a standard tissue culture system).

Some of the features of the present methods may include the production of considerable amounts of pro-inflammatory cytokines (e.g., IL-8 and TNF-$\alpha$) and alkaline phosphatase upon exposure to a human enteric bacterial pathogen; and multi-lineage differentiation of intestinal epithelial cells (i.e., enterocytes (villin), goblet (mucin 2, MUC 2) and M (Sialyl Lewis Antigen) cell lineages). Thus, according to non-limiting example embodiments, the tissue-like differentiation markers may be selected from the group consisting of multi-lineage differentiation of intestinal epithelial cells as well as the production of considerable amounts of pro-inflammatory cytokines (e.g., IL-8 and TNF-$\alpha$) and alkaline phosphatase upon exposure to a human enteric bacterial pathogen.

In example embodiments, the tissue-like markers may be selected from the group consisting of (i) the ability to mimic epithelial tissue monolayer organization, (ii) the induction of appropriate polarity of epithelial cells, tight junctions, desmosomes, E-cadherin and microvilli, (iii) a long-term culture (e.g., up to 28 days or beyond) with high viability of the primary cells, (iv) the transport of nutrients such as glucose (e.g., expression of dissacharidases, and presence of sugar transporters), (v) migration of the lymphocytes through the epithelial cell layer and localization in the extracellular matrix (ECM), and (vi) expansion and differentiation of the intestinal stem cell compartment.

The assaying may further include comparing the measured or observed parameter to a control value of the measured or observed parameter, and wherein the control value corresponds to a measurement of the same parameter for the cell culture before introduction of the pathogen or measurement of the same parameter for a cell culture into which said infectious pathogen has not been introduced.

Figure 5:
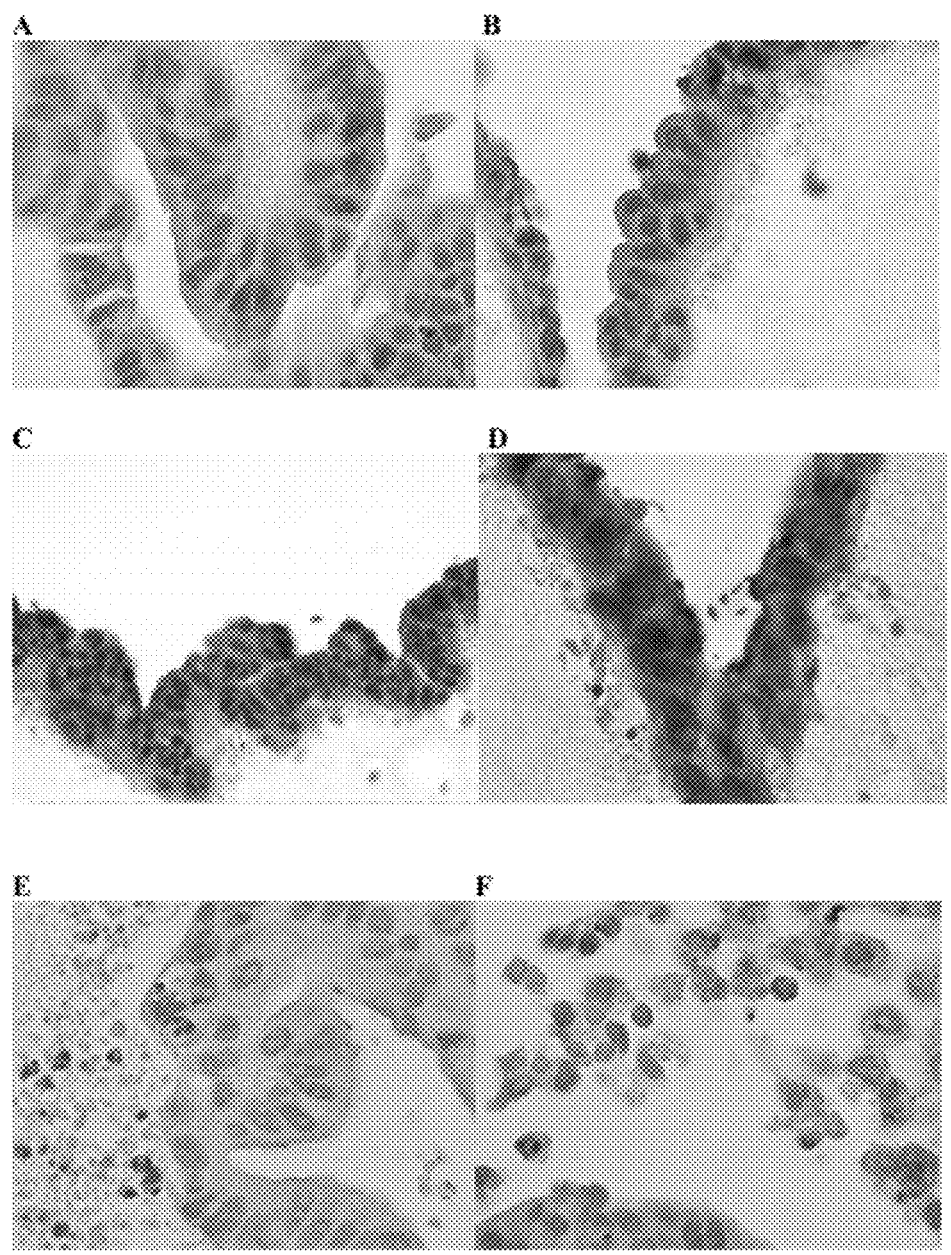
FIG. 5(A-F) depicts immunochemical staining of 17 day-cells cultured in the 3-D microgravity model. Cells were infected with *Salmonella Typhi* and immunochemical stained for *Salmonella* antigens using anti-CSA mAbs.

FIG. 5 depicts immunochemical staining of 17 day-cells cultured in the 3-D microgravity model. Cells were infected with *Salmonella Typhi* and immunochemical staining for *Salmonella* antigens using anti-CSA mAbs before (A) or 1 hour (B), 2 hours (C), 3 hours (D) and one day (E) (F) after infection. 100× magnification.

FIG. 6 depicts immunochemical staining of 12 day-cells cultured in the 3-D microgravity model. Cells were infected with *Shigella flexneri* and immunochemical stained for *Shigella* antigens using anti-*Shigella* mAbs before (A) or 1 hour (B and C) after infection. 100× magnification.

Figure 7:
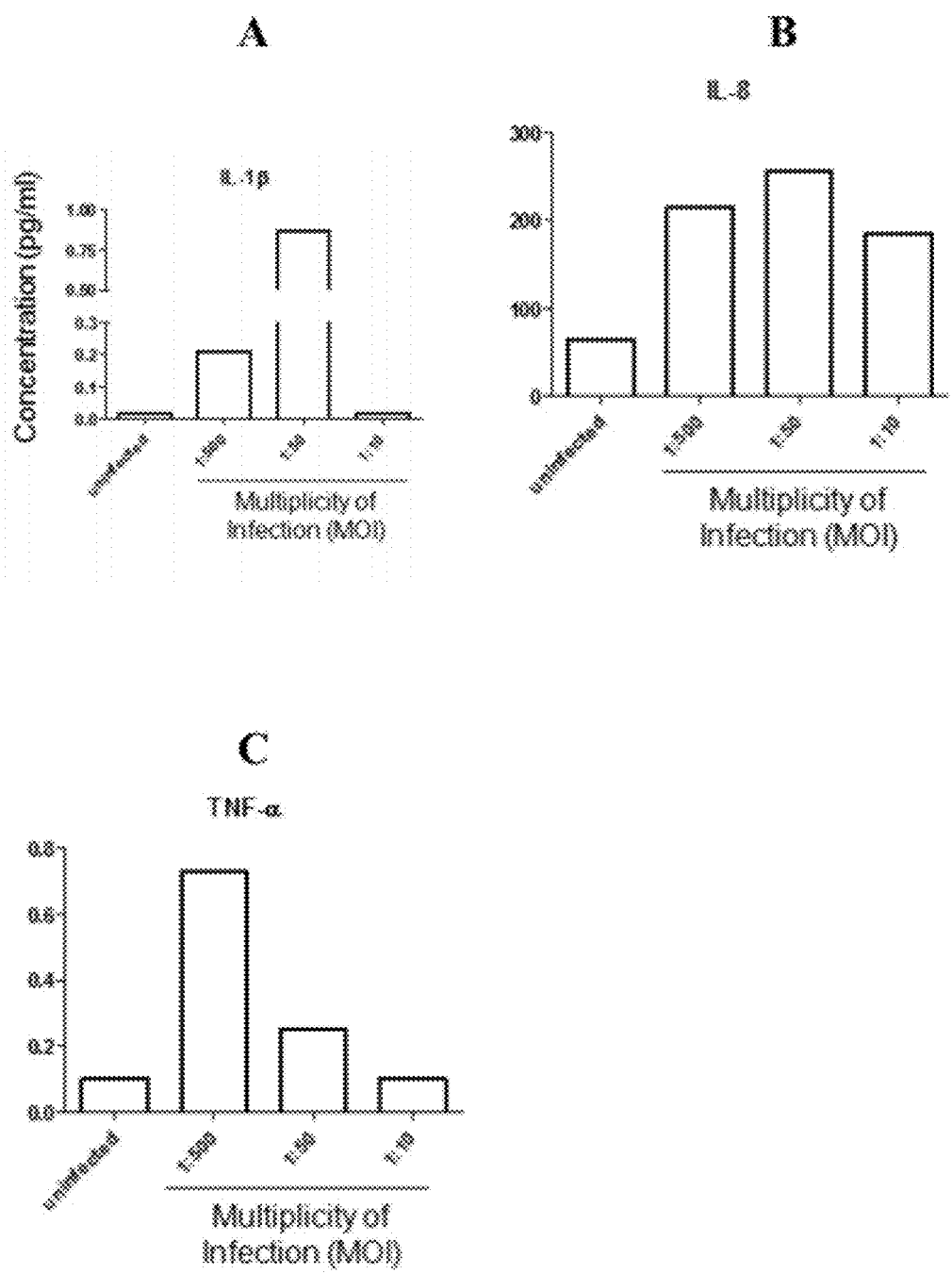
FIG. 7(A-C) depicts cytokine production in organotypic culture supernatants following exposure to *Shigella flexneri*.

FIG. 7 depicts cytokine production in organotypic culture supernatants following exposure to *Shigella flexneri*. Cells from a 15-day 3-D organotypic culture were left uninfected or exposed to *Shigella* at different multiplicity of infection (MOI) and supernatants collected 2 hours after infection. Cytokines were measured by using the CBA multiplex assay.

It is contemplated that the present 3D models may be used e.g., to study probiotics (such as *Escherichia coli* (*E. coli*) strain Nissle 1917 (EcN)) or commensals (such as *E. coli* strain BL21) and their interaction with enteric pathogens.

Figure 8:
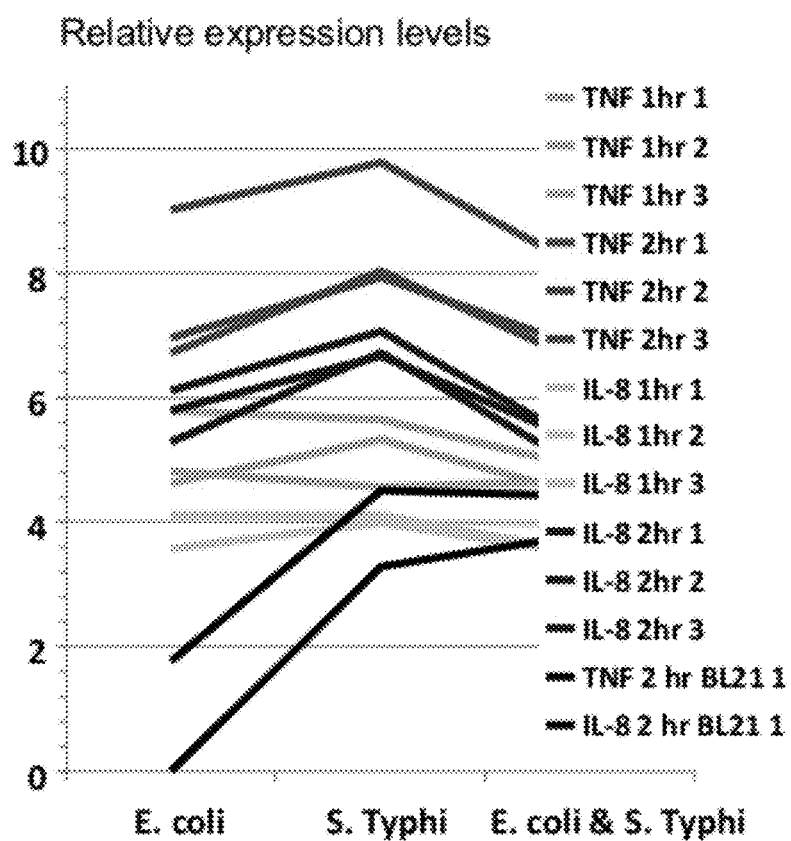
FIG. 8 depicts gene expression level of TNF-α and IL-8 in response to Probiotic *E. coli* Nissle 1917 and the enteric pathogen *Salmonella enterica* serovar *Typhi* (*S. Typhi*).

FIG. 8 depicts gene expression level of TNF-α and IL-8 in response to Probiotic *E. coli* Nissle 1917 and the enteric pathogen *Salmonella enterica* serovar *Typhi* (*S. Typhi*). qRT-PCR mRNA expression levels are presented relative to control cells without bacteria. Time points are indicated by 1 hr or 2 hr, biological replicates by 1, 2 or 3. Expression levels were averaged across the two technical replicates for each biological replicate. Black lines correspond to control experiments with the non-probiotic *E. coli* BL21.

Figure 9:
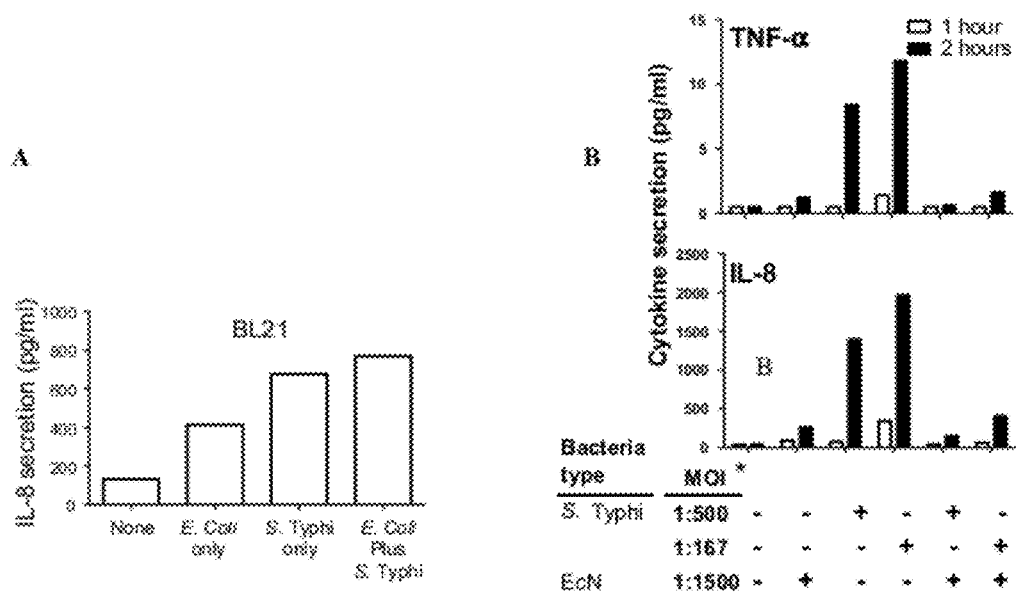
FIG. 9(A-B) depicts anti-bacterial properties of the probiotics in an example of a 3-D model.

FIG. 9 depicts anti-bacterial properties of the probiotics in the 3-D model. Detection of cytokines in the supernatants after 2 hours of exposure to *S. Typhi* (MOI=1:500) and or the control BL21 strain (MOI=1:1500) (A), or after 1 and 2 hours exposure to *S. Typhi* and or *E. coli* Nissle 1917 (EcN) strain (B). *MOI, multiplicity of infection.

The present 3-D models may also be used to study biofilm formation: Some features may include production of mucus by the goblet cells and incorporation of IgA.

Figure 10:
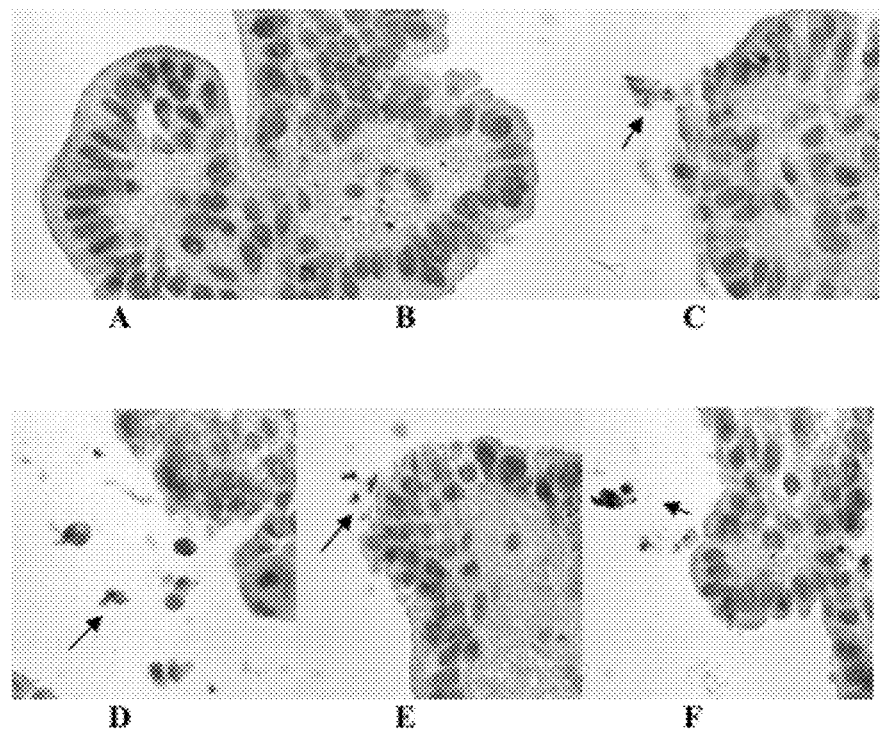
FIG. 10(A-F) depicts immunochemical staining for IgA in cells cultured in the 3-D model.

FIG. 10 depicts immunochemical staining for IgA in cells cultured in the 3-D model. Cells were cultured in media only (A, control) or as single cultures with *E. coli* Nissle 1917 (EcN) (B) or SIgA, (C and D), or as co-culture with EcN and SIgA, (E and F) for 2 hours. 100× magnification.

The present 3-D models may also be used to study human embryonic stem cells (hESCs) differentiation and the presence of primitive gut markers in intestinal cells (e.g., Sox 9)

FIG. 11 depicts the ability to differentiate Stem Cells (e.g., Human embryonic stem cell (hESCs) (e.g., H9 lines)) in the 3-D model. Cells were stained with Sox 9 antibodies which detect Sox9 antigens characteristic of primitive gut epithelial cells. The figure depicts cytoplasmic staining for epithelial cells vs. nuclear staining for Stem Cells (SC) (a). SC differentiation (b): alone (left panel) or as a teratoma (right panel). 100× magnification.

Figure 12:
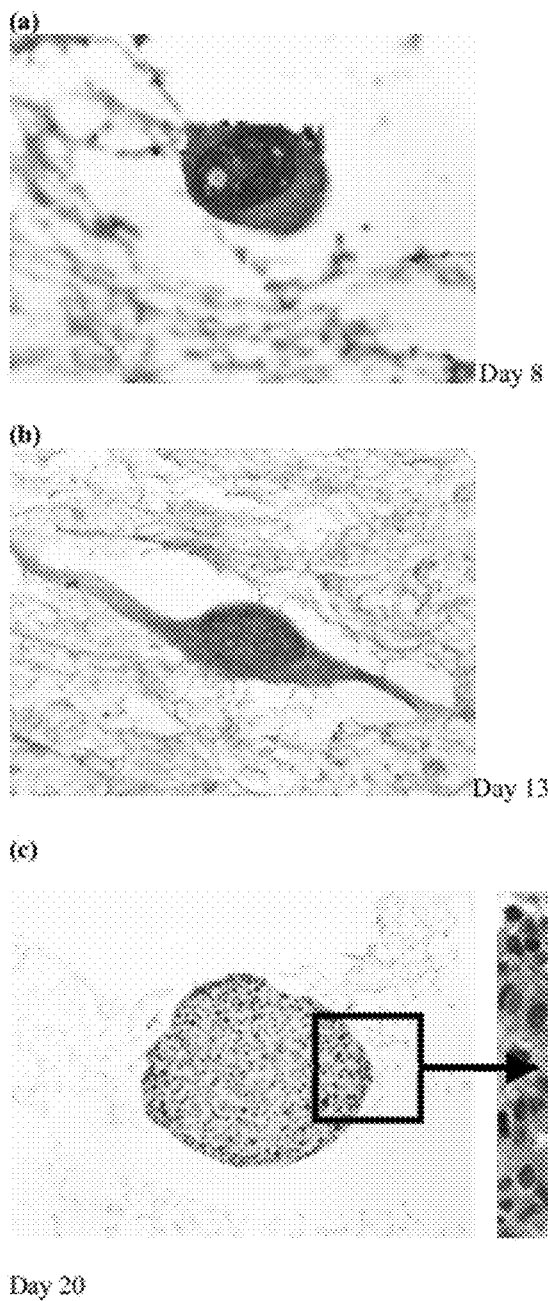
FIG. 12(A-C) depicts the ability to expand Stem Cells in the present 3-D model. Immunochemical staining for the proliferation marker Ki67 on human embryonic stem cell (hESCs) (e.g., H9 lines).

FIG. 12 depicts the ability to expand Stem Cells in the present 3-D model. Immunochemical staining for the proliferation marker Ki67 on human embryonic stem cell (hESCs) (e.g., H9 lines).

Additional embodiments are directed to methods of studying host responses to inflammatory stimuli, which may include preparing a multi-cellular three-dimensional tissue construct (for example according to the methods described herein), introducing agents or soluble factors (e.g., cytokines, chemokines) to the multi-cellular three-dimensional tissue construct; and assaying the effects of inflammatory stimuli on the multi-cellular three-dimensional tissue construct.

Further embodiments are directed to methods of studying intestinal stem cell biology and function in health and disease, which methods may include preparing a multi-cellular three-dimensional tissue construct (e.g., according to the methods described herein), isolation and culture on intestinal crypt cells, using specific markers to identify stem cells in the crypt niche, introducing agents or stimuli to the multi-cellular three-dimensional tissue construct; and assaying the effects of these variables in expansion and differentiation of intestinal stem cells.

It is contemplated that further non-limiting example embodiments may be directed to methods of measuring chemosensitivity of tissues to a toxic material. Such methods may include for example, embedding isolated fibroblasts and isolated endothelial cells in a matrix enriched with one or more gut basement membrane proteins to form a cell-containing matrix; adding the cell-containing matrix to a bioreactor containing epithelial cells and culture medium to form a cell culture; applying microgravity conditions that produce laminar flow and low shear force inside the culture, allowing the cells to culture (e.g., for up to about 24 days), while adding activated lymphocytes to the cell culture, to form a multi-cellular three-dimensional tissue construct comprising an epithelial cell line, lymphocytes, endothelial cells and fibroblasts; and introducing a toxic material to the multi-cellular three-dimensional tissue construct. Example methods further include assaying the chemosensitivity of said toxic material by obtaining a measurement of cell death or damage among cultured cells after introduction of said toxic material; and comparing the measurement to a control value of cell death or damage for a cell culture into which said toxic material has not been introduced.

Also provided herein are kits that may include at least one matrix as described herein and at least one apparatus for performing the methods discussed herein, such as one or more tissue culture flasks, culture plates, and a rotating wall vessel bioreactor. By way of non-limiting example, the matrix that may be included in such a kit may include bovine collagen I enriched with gut basement membrane proteins, such as one or more of laminin, collagen IV, fibronectin and heparan sulfate proteoglycans, or other proteins known to those skilled in the art.

Example kits may also include at least one matrix as described herein (such as collagen I enriched with gut basement proteins) and instructions regarding how to perform one or more of the present methods, and/or how to use such matrix to form the present multicellular 3-dimensional tissue constructs.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXAMPLES

Example 1

In this Example, an example of the present three-dimensional multicellular organotypic model of human intestinal mucosa was formed and infected with *S. Typhi*.

HCT-8 cells (CCL-244, ATCC, Manassas, Va.), a human epithelial cell line derived from the junction of the small and large bowel, (Tompkins WA, Watrach AM, Schmale JD, Schultz R M, Harris J A, "Cultural and antigenic properties of newly established cell strains derived from adenocarcinomas of the human colon and rectum," *J Natl Cancer Inst* 1974; 52:1101-10) was grown in RPMI (INVITROGEN, Carlsbad, Calif.) supplemented with 100 U/ml penicillin (INVITROGEN), 100 µg/ml streptomycin (INVITROGEN), 50 µg/ml gentamicin (INVITROGEN), 2 mM L-glutamine (INVITROGEN), 2.5 mM sodium pyruvate (INVITROGEN), 10 mM HEPES buffer (INVITROGEN) and 10% heat-inactivated fetal bovine serum (ATLANTA BIOLOGICALS, Lawrenceville, Ga.).

CCD-18Co cells (CRL-1459, ATCC), primary human colonic fibroblasts, were grown in Basal Eagle's medium (INVITROGEN) enriched with 100 U/ml penicillin, 100 µg/ml streptomycin, 50 µg/ml gentamicin, 2 mM L-glutamine, 2.5 mM sodium pyruvate, 10 mM HEPES buffer and 10% heat-inactivated fetal bovine serum.

HUVEC cells (CRL-1730, ATCC), human umbilical vein endothelial cells, were grown in F12 medium (INVITROGEN) enriched with 100 µg/mL heparan (SIGMA St. Louis, Mo.), 3 µg/mL Endothelial cell growth supplement (ECGS, MILLIPORE, Bedford, Mass.), and supplement 1 (i.e., 100 U/ml penicillin, 100 µg/ml streptomycin, 50 µg/ml gentamicin, 2 mM L-glutamine, 2.5 mM sodium pyruvate, 10 mM HEPES buffer and 10% heat-inactivated fetal bovine serum.).

Lymphocytes were isolated and cultured as previously described. (R. Salerno-Goncalves et al., *J. Immunol* 169 (4), 2196 (2002).). Blood specimens were collected from healthy volunteers. Peripheral blood mononuclear cells (PBMC) were isolated from the blood by density gradient centrifugation and cryopreserved in liquid $N_2$. Lymphoblasts were generated by incubating PBMC with 1 µg/mL phytohemagglutinin type L (PHA-L, SIGMA) for 24 hours. PHA-stimulated lymphocytes were henceforth called "blasts" (R. Salerno-Goncalves et al., *J. Immunol* 169 (4), 2196 (2002)). More than 90% of these blasts expressed cluster of differentiation (CD)3 antigens on their membrane surface, a phenotype consistent with T lymphocytes.

All cell cultures were grown under standard culture conditions, i.e., at 37° C. in an atmosphere of 5% $CO_2$.

Development of the 3-D Organotypic Model of the Human Intestinal Mucosa.

The three cell types, HCT-8, CCD-18Co and HUVEC cells, were initially grown as standard monolayers in tissue culture flasks (BD PHARMINGEN, San Diego, Calif.), containing the media described above. Cells were washed twice in phosphate-buffered saline (PBS) and detached from the flasks by trypsin, 0.25% (1×) with EDTA 4Na (INVITROGEN) treatment. For CCD-18Co and HUVEC cells, cells were then resuspended in DMEM-30% FBS medium and added to an enriched collagen mixture at a density of 1.0-1.2 and 1.5-2.0×$10^6$ cells/mL for HUVEC and CCD-18Co cells, respectively. In some cases stem cells can also be incorporated into the enriched collagen mixture. In these cases, the stem cells may be first expanded in plates in the presence of the mouse embryonic fibroblasts (MEFs) and stem cell media (i.e., DMEM-F12 Medium (INVITROGEN) supplemented with 25% of Knockout Serum Replacer (INVITROGEN), 1% L-Glutamine (INVITROGEN), 2.5% Non-Essential Amino Acids (INVITROGEN) and 2 µg/ml Basic FGF solution (Sigma) and then incorporated with the collagen mixture. The collagen mixture may be composed of DMEM (INVITROGEN), supplemented with 50 µg/mL gentamicin, 2 mM L-glutamine and 10% heat-inactivated fetal bovine serum plus 3 mg/mL bovine collagen-I (INVITROGEN), 10 µg/mL laminin (SIGMA), 40 µg/mL collagen IV (SIGMA), 10 µg/mL fibronectin (BD PHARMINGEN), 2 µg/mL heparan sulfate proteoglycan (SIGMA) and 15 mM NaOH (to reach the physiological pH). Four to five milliliters of this mixture were subsequently added to each 6 well-millicell culture plate insert (Millipore), previously loaded into 6 well-plates, and allowed to jellify in the hood. After 1 hour, the 6-well plates were transferred to a 37° C., 5% $CO_2$ incubator for 1-2 additional hours. Then, the cell-containing gel were aseptically cut in small squares (~5×5 mm) and transferred into 50-mL rotating wall vessels (RWV) (SYNTHECON, Houston, Tex.) containing 3-D culture media: Ham's F-12 (INVITROGEN) supplemented with 5 µg/mL insulin (SIGMA), 0.4 µg/mL 3,3',5-triiodo-L-thyronine (T3, SIGMA), 1.8×$10^{-4}$ M adenine (SIGMA), 5 µg/mL transferrin (SIGMA), $10^{-10}$ (M cholera toxin (SIGMA), 2 mM L-glutamine, 4 ng/mL Leukemia Inhibitory Factor human (LIF, Santa Cruz Biotechnology, Santa Cruz, Calif.), 5 ng/mL Stem Cell Factor (Sigma), 10 ng/mL Endothelin 3 human (Sigma) and 5 ng/mL Fibroblast Growth Factor (SIGMA). (Young GP, Morton CL, Rose IS, Taranto TM, Bhathal P S. "Effects of intestinal adaptation on insulin binding to villus cell membranes," Gut 1987; 28 Suppl:57-62) HCT-8 epithelial cells, after trypsinization, were resuspended in DMEM-30% FBS medium at a density of $10^7$ cells/mL and 1 mL added to vessels with cell-containing gels. The vessels were then incubated at 37° C., 5% $CO_2$ under microgravity provided by the RWV bioreactor (SYNTHECON). About 20 mL of 3-D culture media were exchanged at 2-3 day intervals. After 4 days (±1 day), activated lymphocyte blasts (2×$10^7$/vessel) were added to each vessel and grown for an additional 5 days (±1 day). At that time, blasts (2×$10^7$/vessel) were added once again to each vessel and cultures continued for up to 12 additional days.

Antibodies for Immunohistochemistry

The following primary anti-human antibodies were used for immunohistochemistry: a mouse anti-CD31 monoclonal antibody (clone 1A10, 1:50, INVITROGEN, Carlsbad, Calif.), a mouse antiCD45 monoclonal antibody (clone 2B11/PD7-26,1:50, DAKO, Carpinteria, Calif.), a rabbit anti-cleaved caspase-3 polyclonal serum (Asp175, 1:100, Cell Signaling Technology), a biotin-labeled goat anti-common *Salmonella* antigen polyclonal antiserum (CSA-1, 1:20, KLP, Gaithersburg, Md., USA), a mouse anti-cytokeratin monoclonal antibody (clone AE1/AE3, 1:100, DAKO), a mouse anti-E-cadherin monoclonal antibody (clone 36B5, 1:20, VECTOR, Burlingame, Calif.), a rabbit anti-Ki-67 monoclonal antibody (clone SP6, 1:50, VECTOR), a mouse anti-MUC-2 monoclonal antibody (clone CCP58, 1:100, INVITROGEN), a rabbit anti-Sodium Glucose Co-transporter-1 (SGLT-1) antiserum (1:3000, MILLIPORE), a mouse anti-Sialyl Lewis Antigen monoclonal antibody (clone C241:5:1: 4, 1:50, VECTOR), a rabbit anti-Sucrase-isomaltase, intestinal (SI) antiserum (1:500, SIGMA), a mouse anti-villin monoclonal antibody (clone CWWB1, 1:30, VECTOR), a mouse anti-vimentin monoclonal antibody (clone V9, 1:200, VECTOR) and a rabbit anti-ZO-1 antiserum (1:100, INVITROGEN).

Preparation of 3-D Constructs for Histology and Immunohistochemistry

The constructs were removed from the vessels and immersed in 5% paraformaldehyde in PBS. After an overnight fixation at 4° C., the constructs were embedded in paraffin-blocks, and 5 µm sections cut and dried in an oven at 37° C. overnight. The sections were then consecutively washed 2 times for 5 minutes in Histo-Clear (NATIONAL DIAGNOSTICS, Atlanta, Ga.), in 95% ethanol and in 75% ethanol to remove the paraffin, and finally rehydrated in PBS for 10 min. For histological staining, tissue sections were stained with hematoxylin and eosin (H&E) and examined under a light microscope for morphological evaluations.

For immunochemical staining for biotin-labeled anti-CSA-1 antibodies, tissue sections were washed in distilled $H_2O$ for 5 minutes, and then treated with PBS containing 3% $H_2O_2$ for 15 minutes at room temperature to block endogenous peroxidase activity. Tissue sections were then washed in PBS/0.5% Tween-20 and blocked with 2.5% normal horse serum to reduce nonspecific staining. After 20 minutes, excess of blocking buffer is blotted and the sections incubated with PBS/0.5% BSA-diluted biotin-labeled anti-CSA-1 antibody for 1 hour at room temperature. After incubating 2 times in PBS/0.5% Tween-20 for 5 minutes each, detection of the primary antibody was performed by staining the sections with Vectastain Elite ABC Kit (Vector) for 5 minutes at room temperature Immunostaining was visualized using 3,3diaminobenzidine (DAB) peroxidase-chromogen reaction (ImmPACT DAB kit, Vector).

For all others immunochemical staining procedures, tissue sections were rinsed in water and the antigen retrieved by autoclaving samples (120° C., 30 seconds) (Pascal chamber, DAKO) in sodium-citrate buffer (INVITROGEN). After washing in distilled $H_2O$ for 5 minutes, the sections were treated with PBS; 3% $H_2O_2$ for 15 minutes at room temperature. Tissue sections were then washed in PBS/0.5% Tween-20 and blocked with blocking buffer (PBS/0.5% Tween-20/5% BSA) to reduce non-specific staining. After 30 minutes, excess of blocking buffer was blotted and the sections incubated with blocking buffer-diluted primary antibody for 1 hour at room temperature. After incubating 2 times in PBS/0.5% Tween-20 for 5 minutes, detection of the primary antibody was performed by incubating the sections with anti-Mouse/Rabbit horseradish peroxidase-labeled antibody (ImmPRESS Universal Antibody Kit, VECTOR) for 30 minutes at room temperature. Immunostaining was visualized using DAB peroxidase-chromogen reaction (ImmPACT DAB kit, VECTOR).

All sections were counterstained with Mayer's hematoxilin (5 minutes), dehydrated, mounted using Histomount (INVITROGEN) and visualized with a Nikon E800 microscope using SPOT software.

Intestinal Enzyme Assays

The constructs were removed from the vessels and gently washed twice with PBS. The constructs were then re-suspended in 500 μl PBS in 1.5 ml tubes and centrifuged at 10,000×g for 15 min at 4° C. to obtain a cell lysate. Cell lysates were kept at −20° C. until assayed. An aliquot of each clarified lysate may be used to detect the presence or activity of intestinal enzymes, e.g., alkaline phosphatase and disaccharidase. The presence of alkaline phosphatase was measured by an ELISA Amplification System (INVITROGEN) which is designed to quantify the amount of color generated by a given quantity of immobilized alkaline phosphatase in the nicotinamide adenine dinucleotide phosphate (NADPH) substrate. The disaccharidase activity was detected by measuring the amount of glucose inside the cells. The QuantiChrom Glucose Assay kit (BIOASSAY SYSTEMS, Hayward, Calif.), which involves a specific color reaction with glucose (i.e., o-toluidine method), was used to determine disaccharidase activity. Both assays were performed according to the manufacturer's instructions.

S. Typhi Infection

Organotypic constructs were infected by incubating them for 3 hours at 37° C. in RPMI (without antibiotics) in the presence of S. Typhi strain ISP1820 (obtained from Dr. J. Nataro, Center for Vaccine Development), at a multiplicity of infection (Mal) of 1, 500:1. (R. Salemo-Goncalves, et al., *J. Immunol*, 169(4), 2196 (2002), R. Salemo-Goncalves, et al., *J. Immunol*, 170(5), 2734 (2003), R. Salemo-Goncalves, et al., *J. Immunol*, 173(9), 5852 (2004), and R. Salemo-Goncalves, et al., *J. Immunol*, 73(6), 3521 (2005)). After incubation, cells were washed and incubated overnight at 37° C. in media containing gentamicin (100 μg/ml) to kill and remove extracellular bacteria.

Cytokine Production after S. Typhi Infection

Levels of interferon (IFN)-γ, interleukin (IL)-1β, IL-6, IL-4, IL-8, IL-10, IL-11, IL-12p70, IL-17a, IL-21, transforming growth factor (TGF)-β and tumor necrosis factor (TNF)-α by the 3-D constructs were measured by a flow cytometry-based multiplex BD Cytometric bead array (CBA). The supernatants were harvested at early (e.g., 1, 2 and 3 hours) and at late time points (e.g., 1 and 2 days) after addition of S. Typhi to the cultures and kept at −70° C. until assayed. In these studies, uninfected cells (medium only) were used as negative controls. CSA assays were carried-out following the manufacturer's instructions. The levels of sensitivity for the various cytokines ranged from 2.5-20 pg/ml.

Example 2

Figure 13:
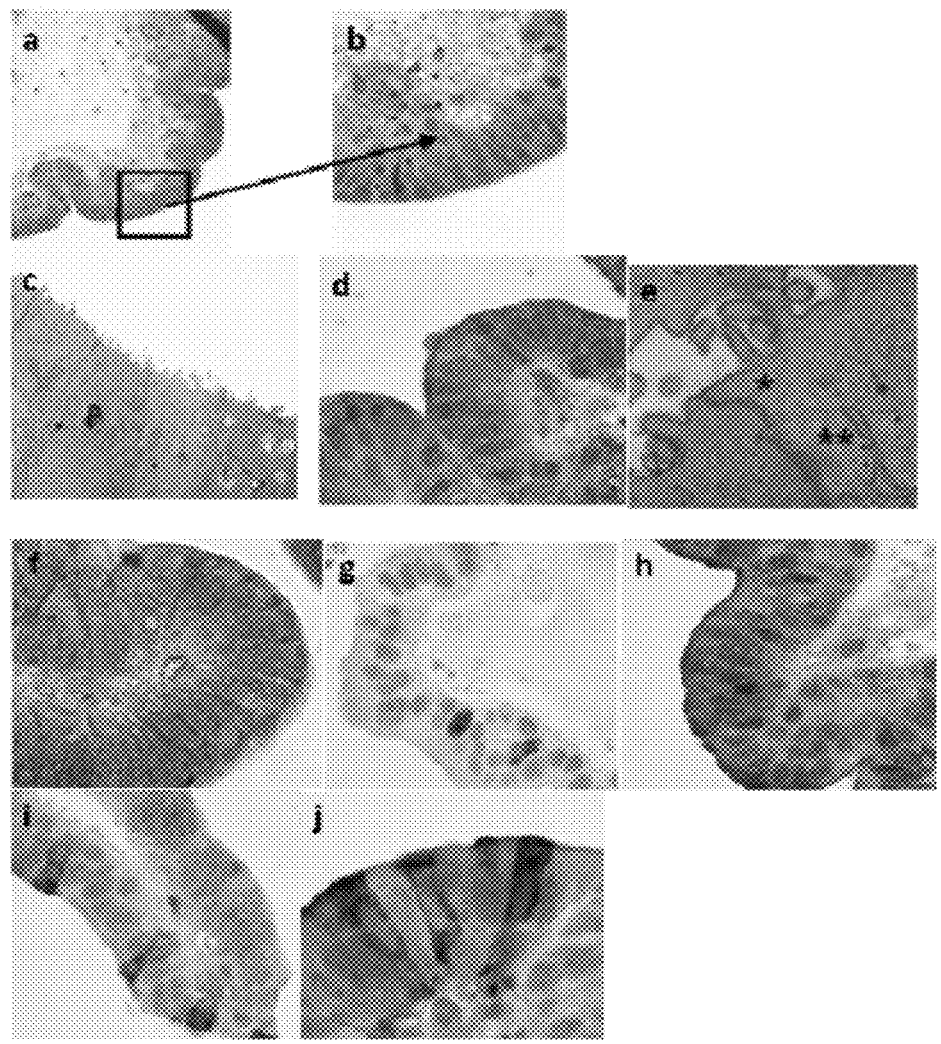
FIG. 13(A-J) depicts epithelial cell differentiation in the present model.

A three-dimensional multicellular organotypic model of human intestinal mucosa was formed as in Example 1, with activated lymphocytes being added twice to the culture at days 4 (±1 day) and 9 (±1 day). After 10 to 15 days, histological staining and electron microscopy demonstrated the presence of villus-like structures in the constructs. About 60-80% of these epithelial cells were organized as a monolayer of polarized cells with nuclei located in a basal position near the ECM, a major feature of well-differentiated cells (See FIG. 13). As shown in this example, the present invention advantageously has cell polarity. FIG. 13(a) demonstrates epithelial cell polarization according to the present embodiments.

FIG. 13 demonstrates epithelial cell differentiation in the present example. Hematoxylin and eosin (H&E) staining of 14 day-cells cultured in the 3-D microgravity model: tissues were stained purple and scaffold stained pink. Lower (a) and higher magnification (b) shows the presence of polarized epithelial cells with microvilli seen collectively as a fuzzy fringe in the apical surface of the epithelium. (FIG. 13b). The presence of microvilli was further confirmed/evidenced by immunochemical staining using the anti-villin mouse mAb and by electron microscopy (FIG. 13c). Assessment by immunostaining for zonula occludens (ZO)-1 polyclonal rabbit antiserum (d), a protein involved in the formation of tight junctions, and electron microscopy (e) demonstrated that the present 3-D organotypic model recapitulates the formation of tight junctions and desmosomes (FIGS. 13d and 13e, (tight junctions (*) and desmosome (**)).

Because immortalized epithelial cells in 3-D systems may lose the growth pattern found in the normal epithelium, the inventors assessed the expression of E-cadherin and the Ki-67 proliferation marker in the present 3-D model. As expected, HCT-8 cell lines expressed E-cadherin but only negligible amount of Ki-67 antigen, a pattern consistent with normal highly-differentiated epithelium (FIGS. 13f and g) Immunochemical staining was used to detect E-cadherin using the anti-E-cadherin mouse mAb. (FIG. 130. The presence of proliferating cells was detected at day 5 and day 15 by using the anti-Ki67 rabbit mAb. (FIG. 13g).

Finally, these HCT-8 cells also expressed numerous markers for multi-lineage differentiation to goblet (mucin 2, MUC 2) and M (Sialyl Lewis Antigen) cell lineages (FIGS. 13h, i and j). The presence of multi-lineage differentiation was observed, microvilli using the anti-villin mouse monoclonal antibody, clone CWWB1, (FIG. 13h); goblet cells using the anti-MUC-2 monoclonal antibody, clone CCP58 (i), and M cells using the anti-Sialyl Lewis Antigen mAb, clone C241: 5:1:4 at day 15. (FIG. 13j). Goblet and M cells were distributed throughout the epithelial layer (FIGS. 13i and j, respectively).

Cells from a 17-day 3-D organotypic culture were also stained by immunochemistry for lymphocytes using the anti-CD45 mAb (low magnification), for endothelial cells using the anti-CD31 mAb (sprouting) (vessel-like conduit formation) (high magnification), and for fibroblasts using the anti-vimentin mAb at low (spindle shaped rounded-fat cell-like shaped) at high magnification.

Evaluation of Intestinal Enzymes

A key element of differentiated and functional enterocytes is the presence of brush border enzymes that are embedded in their microvilli, rather than free in the intestinal lumen. The presence of two intestinal brush border enzymes was evaluated in the present 3-D organotypic model: alkaline phosphatase and disaccharidase. Alkaline phosphatases (APs) are enzymes involved in the breakdown of dietary lipids, as well as, in dephosphorylation of the lipid moiety of LPS of the GRAM negative bacteria. In the present 3-D model, APs were detected in clarified cellular homogenates by ELISA. The present inventors observed that 12-days later after exposure to *S. Typhi*, higher AP activity was present in *S. Typhi*-infected cultures when compared with non-infected cultures.

TABLE 1

Presence of alkaline phosphatase in the lysate of cells cultured in presence or absence of *Salmonella Typhi*

| Experiment # | Infection | Alkaline Phosphatase (ng/ml) |
| --- | --- | --- |
| 1 | none | 48.3 |
|   | Salmonella | 133.5 |
| 2 | none | 55.7 |
|   | Salmonella | 126.5 |

Figure 14:
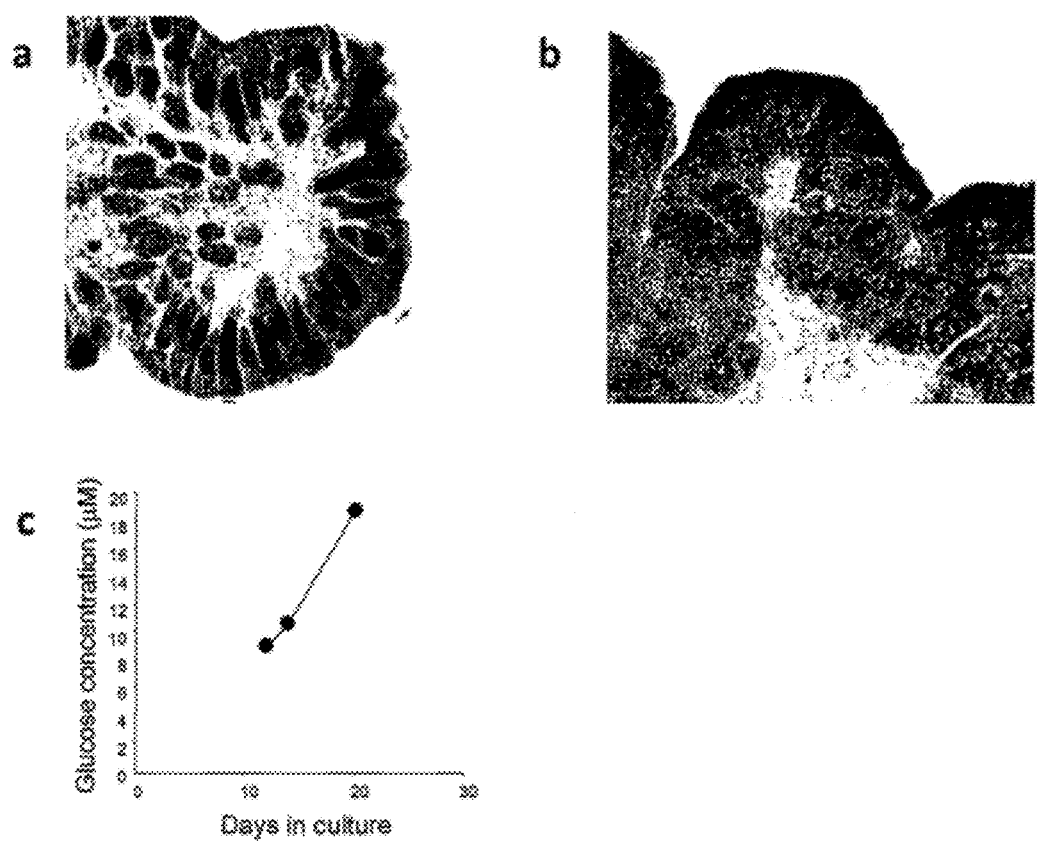
FIG. 14(A-C) depicts an evaluation of glucose metabolism.

The present inventors also investigated the presence of the machinery for the specific digestion and transfer of glucose. Intestinal sugar delivery depends on the levels of expression of dissacharidases (i.e., sucrase isomaltase, SI) and sugar transporters. Glucose is actively transported across the apical brush border into enterocytes by the sodium-glucose co-transporter 1 (SGLT1) 1. The SI enzyme is the most abundant of the dissacharidases, accounting for approximately 10% of the intrinsic proteins in the brush border. Sucrase isomaltase is responsible for all of the sucrase activity, for approximately 90% of the isomaltase activity, and for 70-80% of the maltase activity of the small intestine. Thus, the present inventors studied the expression of intestinal dissacharidases associated with enterocytes brush border membrane in the present 3-D model by immunochemical staining for SI enzymes. The expression of sodium-glucose co-transporter 1 (SGLT1) was also studied by immunochemical staining. The inventors observed apical expression of dissacharidases (i.e., sucrase-isomaltase, SI) and sugar transporters (i.e., energy-dependent sodium-glucose co-transporter 1, SGLT1) which strongly suggests that epithelial cells in the present 3-D model are able to absorb and transport glucose (FIG. 14) The disaccharidase activity was also measured in the cell lysates. The disaccharidase activity was detected by measuring the amount of glucose inside the cells using the classical o-toluidine method (See K. M. Dubowski, *Clin Chem* 8, 215 (1962). As shown in FIG. 14c, glucose levels in cultures maintained for 12 to 20 days were found to increase over time. These results are in agreement to previous work showing that glucose transport increases with time in culture. (H. M. Carvalho, et al., Cell Microbiol. 7 (12), 1771 (2005). Finally, these results provide another independent indication that cells in the organoid cultures remain functional.

These results demonstrate a remarkable degree of differentiation of HCT-8 epithelial cells in the present 3-D model.

Assessment of Cell Viability

Figure 16:
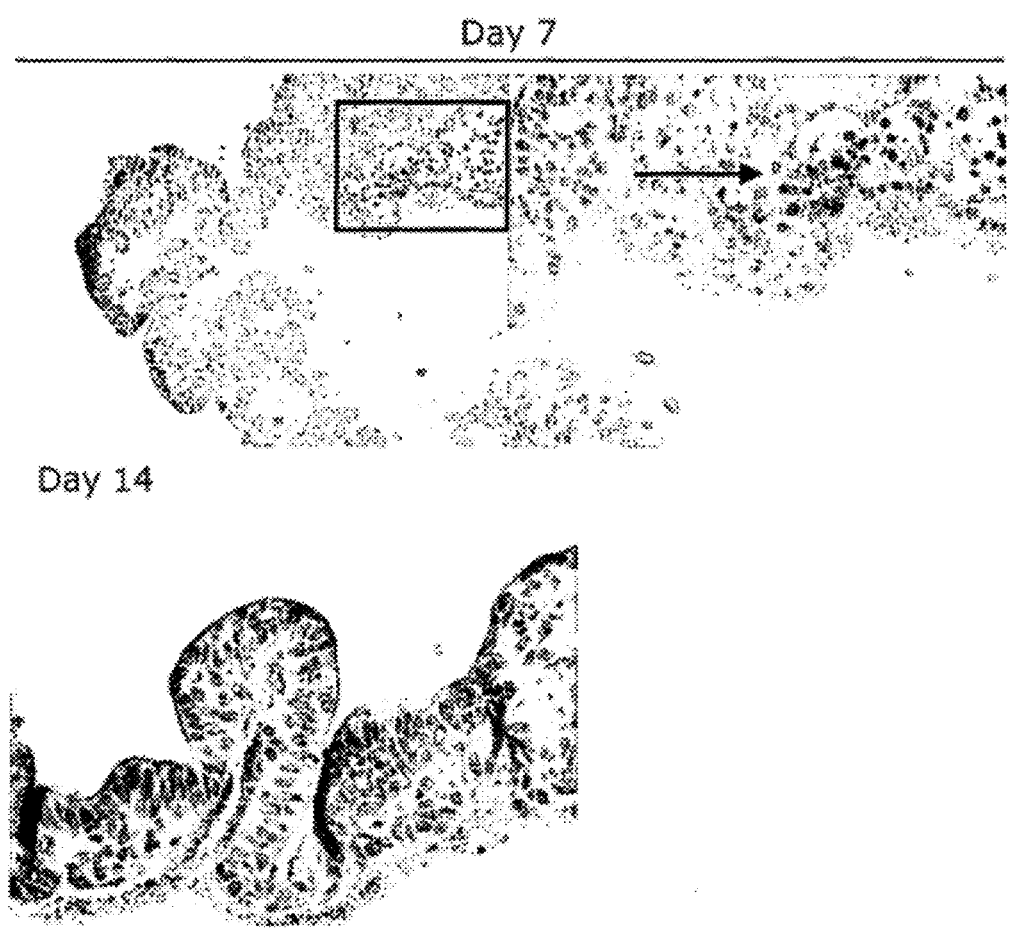
FIG. 16 depicts the detection of apoptotic cells using immunochemical staining for cleaved Caspase-3.

An important measurement to assess the potential of this model for long-term studies is to study cell viability. Several studies have demonstrated that good viability for primary cells lasting more than 10 days in culture systems has been difficult to achieve. (N. Perreault and Beaulieu, *Exp Cell Res*, 245 (1), 34 (1998)). In the present organotypic model, the viability of fibroblasts and endothelial cells remained very high even after 4 weeks in culture, which is remarkably similar to the reported 18-57 days of turnover time of the small intestine mucosa in vivo (Cheng et al., *Am J Anat*, 126 (4) 507 (1969), and H. Ireland et al. *Dev Dyn* 233 (4), 1332 (2005) (data not shown). The apoptotic cells, when present, were mainly in the apoptotic cores located just below the epithelial layer. These apoptotic cores have the tendency to decrease as the cells move along the differentiation path (FIG. 16). In addition, lymphocytes remain alive for at least 6 days (last day examined) in culture.

The present inventors also examined the presence and persistence of other cell types by monitoring the presence of defined cellular markers for each individual cell type (i.e., CD45 for hematopoietic-derived cells, including lymphocytes; CD31 for endothelial cells and Vimentin for fibroblasts). These studies were performed by immunochemistry. The inventors observed that the lymphocytes migrated through the epithelial cell layer and localized to the ECM. The inventors were able to detect lymphocytes for at least 7 days (last day examined) (See FIG. 15)

Figure 15:
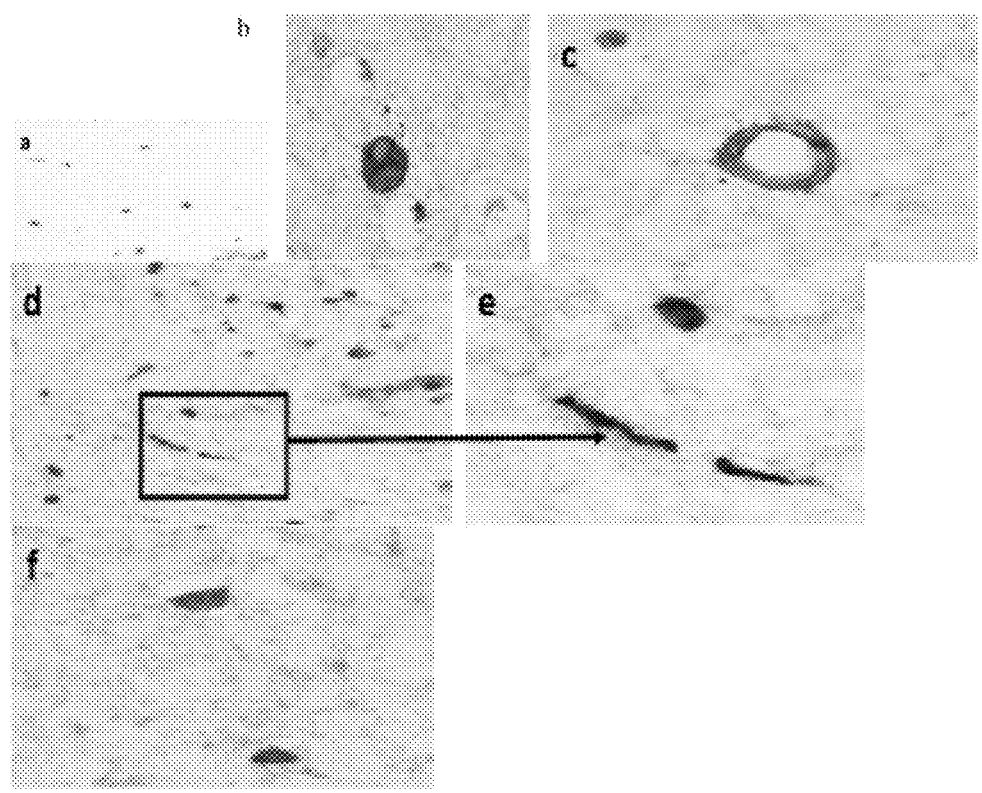
FIG. 15(A-F) depicts the incorporation of multiple cell types in the extracellular matrix of the present model.

FIG. 15 depicts the detection of lymphocytes, endothelial cells and fibroblasts in the extracellular matrix. Cells from a 17-day 3-D organotypic culture were stained by immunochemistry for lymphocytes using the anti-CD45 monoclonal antibodies, clones 2B11 and PD7/26 (a) (low magnification), for endothelial cells using the anti-CD31 monoclonal antibody, clone 1A10 (b) (c) (high magnification), and for fibroblasts using the anti-vimentin monoclonal antibody, clone V9 (Low (d) and high (e) (f) magnification.)

As in the native gut tissue, in the present 3-D model fibroblasts and endothelial cells remained dispersed throughout the ECM. Interestingly, the inventors observed that individual endothelial cells exhibited cytoplasmic extensions that form bridges between them, suggesting that these endothelial cells were activated and underwent a remodeling phase (See FIGS. 15b and 15c). However, the vast majority of these endothelial cells do not appear to differentiate towards the formation of vessel-like conduits. Additional studies may be useful in further determining conditions that will further enable vessel-like conduits to form. Interestingly, fibroblasts showed different shapes, ranging from classical spindle shaped to rounded-fat cell-like shaped with the nucleus pushed to one side (See FIGS. 15d, e and f). These results suggest that cells were activated and remain able to both receive and respond to differentiation signals.

Finally, several studies have demonstrated that good viability for primary cells lasting more than 10 days in culture systems is difficult to achieve. (See Perreault N, Beaulieu J F, "Primary cultures of fully differentiated and pure human intestinal epithelial cells," *Exp Cell Res* 1998; 245:34-42.) Thus, the present inventors assessed cell viability by immunochemical staining using antibodies to cleaved Caspase-3.

Up to 20 days after the initiation of the cultures, few cleaved Caspase-3-positive cells were observed in the ECM, the major location of primary cells including lymphocytes, fibroblasts and endothelial cells (FIG. 16).

Example 3

Cytokine Secretion in the 3-D Organotypic Model Under Different Culture Conditions (e.g., *S. Typhi*-Infected and Uninfected Cultures)

Although the combination of the features described above give some insights into the similarities of the present 3-D organotypic model to in vivo tissues, the inventors further assessed its functionality by observing its response to exposure to a human enteric bacterial pathogen. Specifically, the inventors examined the changes in the epithelial cell morphology, as well as cytokine production, following exposure to wild-type *Salmonella enterica* serovar *Typhi* (*S. Typhi*) strain ISP1820, to evaluate whether it mimicked the reported stages of the infection.

The identification and characterization of *S. Typhi*-infected cells was accomplished using a polyclonal antibody that specifically detects common *Salmonella* antigens (CSA-1). A visible feature of the *Salmonella* entry process in vivo, i.e., membrane rearrangements or ruffles, were observed in the present system as early as 1 hour after infection (See FIG. 5) and increased over time (FIG. 17). Of note, these ruffles were absent in the control one day after infection, the ruffles fade away and bacteria, when present, was mostly observed on the cell surface/brush border of healthy looking epithelial cells or intracellular in epithelial cells sloughed from the monolayer which likely died as a result of the infection (FIGS. 5E and F).

Because several cytokines, such as interleukin (IL)-10, IL-12, tumor necrosis factor (TNF)-α and interferon (IFN)-γ are likely to be important components of resistance to *Salmonella* infection in humans, it was of importance to evaluate the effect of *S. Typhi* on cytokine production in the current 3-D model. The levels of IFN-γ, IL-1β, IL-6, IL-4, IL-8, IL-10, IL-11, IL 12p70, IL-17a, IL-21, TGF-β and TNF-α were measured in the present 3-D model by using a flow cytometry-based multiplex BO Cytometric bead array (CBA). The inventors also observed that the exposure to *Salmonella* resulted in production of cytokines, including IL-1β, IL-6, IL-8, IL-11, IL-12p70, IL-17a, IL-21 and TNF-α (FIGS. 17*a* and *b*).

FIG. 5 depicts changes in epithelial cell morphology and cytokine production in organotypic culture supernatants following exposure to *Salmonella enterica* serovar *Typhi* (*S. Typhi*). Cells from a 14-day 3-D organotypic culture were left uninfected or exposed to *S. Typhi* and supernatants collected 1 hour, 2 hours, 3 hours (A), or 1 day, 2 and 3 days after infection at different Multiplicity of infection (MOI) (B). Cytokines were measured by using the CBA multiplex assay The inventors detected cytokine secretion at early (e.g., 1, 2 and 3 hours) and at later time points (e.g., 1 and 2 days) after addition of *S. Typhi* to the cultures. Non-infected cells (medium only) were used as negative controls in these studies. Increases in cytokine secretion occur rapidly after infection with *S. Typhi*. High levels of cytokines such as IL-1β, IL-11, IL-12p70, IL-17a, IL-21 and TNF-α were seen within 1-2 hours after infection, peaking by 3 h and declining afterwards, approaching baseline values 1 day after infection (FIG. 5*a* and *b* and FIG. 17*a* and *b*).

Interestingly, at later times (e.g., 1-2 days) after exposure to *S. Typhi*, high levels of IL-6, IL-8 cytokines as compared with negative controls were observed in culture supernatants (FIG. 17*b*). This phenomenon was found to be dose-dependent (data not shown). It is likely that transient signals provided by cytokines released within a few hours after infection play an important role in initiating and regulating the production of IL-6 and IL-8 cytokines. After 1-2 days, all other cytokines remained at levels below assay detection or the differences between experimental and controls were no longer evidenced.

These results are in agreement, and further demonstrate the importance of these cytokines in the control of *Salmonella* infection (See Kagnoff M F, Eckmann L., "Epithelial cells as sensors for microbial infection," *J Clin Invest* 1997; 100:6-10; Raffatellu M, Santos R L, Verhoeven D E, George M D, Wilson R P, Winter S E, Godinez I, Sankaran S, Paixao T A, Gordon M A, Kolls J K, Dandekar S, Baumler A J, "Simian immunodeficiency virus-induced mucosal interleukin-17 deficiency promotes *Salmonella* dissemination from the gut," *Nat Med* 2008; 14:421-8) and further confirm the functional capacity of this 3-D organotypic model to properly react to the presence of an enteric pathogen.

To summarize, although 3-D approaches have been attempted by other investigators, the present system provides major innovations and advances, such as use of a matrix enriched with gut basement membrane proteins. Also, to the present inventors' knowledge, except for their present system described herein, attempts to integrate multiple cell types in 3-D constructs grown under microgravity have been unsuccessful. Finally, the present inventors provided evidence herein that their present 3-D model may be a helpful tool to investigate the early events of the host interaction with gastrointestinal pathogens, including invasion, pathogenesis and immune responses.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of preparing a multi-cellular three-dimensional construct, comprising
    growing human intestinal epithelial cells, primary human umbilical vein endothelial cells (HUVEC), and primary human fibroblast cells separately as two-dimensional (2-D) confluent monolayers;
    embedding the fibroblast cells and the endothelial cells, in a collagen-I extracellular matrix mixture enriched with gut basement membrane proteins comprising laminin, collagen IV, fibronectin and heparin sulfate proteoglycan, to form a cell-containing gel; with a specific gravity similar to culture medium;
    adding the cell-containing gel to a rotating wall vessel bioreactor and suspending the human intestinal epithelial cells in medium and then adding the suspended cells to the rotating wall vessel to form a cell culture; and
    applying microgravity conditions that produce laminar flow and minimize shear force inside the culture, allowing the cells to culture, while adding primary human lymphocytes to the cell culture, to form a multi-cellular three-dimensional tissue construct; wherein the epithelial cells form a simple columnar epithelium and differentiate into multiple lineages.

2. The method of claim 1, wherein the multi-cellular three-dimensional tissue construct comprises a multi-cellular three-dimensional organotypic model of human intestinal mucosa.

3. The method of claim 1, wherein the epithelial cells comprise a HCT-8 human enterocyte intestinal epithelial cell line derived from the junction of the small and large bowel.

4. The method of claim 1, further comprising embedding stem cells in the collagen I matrix in forming the cell-containing gel.

5. The method of claim 1, wherein the cells are allowed to culture for up to about 24 days.

6. The method of claim 1, wherein the lymphocytes are added to the cell culture at around day 3-5 of the culture and at around day 8-10 of the culture.

7. The method of claim 1, wherein said primary human fibroblast cells comprise primary human CCD-18Co cells.

8. A method of preparing a multi-cellular three-dimensional tissue construct, comprising growing human intestinal epithelial, primary human umbilical vein endothelial cells (HUVEC), and CCD-18Co primary human fibroblast cells separately as two-dimensional (2-D) confluent monolayers, wherein the human intestinal epithelial cells comprises a HCT-8 human intestinal epithelial cell line;

embedding the fibroblast cells and the endothelial cells, in a collagen-I extracellular matrix mixture enriched with gut basement membrane proteins comprising laminin, collagen IV, fibronectin and heparin sulfate proteoglycan, at a concentration of $1.0$-$1.2 \times 10^6$ and $1.5$-$2.0 \times 10^6$ cells/mL for HUVEC and CCD-18Co cells, respectively, to form a cell-containing gel; with a specific gravity similar to culture medium;

adding the cell-containing gel to a rotating wall vessel bioreactor and suspending said HCT-8 human intestinal epithelial cells in medium and then adding the suspended cells at a concentration of about $10^7$ cells/mL to the rotating wall vessel to form a cell culture; and applying microgravity conditions that produce laminar flow and minimize shear force inside the culture, allowing the cells to culture, while adding primary human lymphocytes to the cell culture, to form a multi-cellular three-dimensional tissue construct; wherein the epithelial cells form a simple columnar epithelium and differentiate into multiple lineages.

* * * * *